US008046053B2

(12) United States Patent
Foley et al.

(10) Patent No.: US 8,046,053 B2
(45) Date of Patent: *Oct. 25, 2011

(54) SYSTEM AND METHOD FOR MODIFYING IMAGES OF A BODY PART

(76) Inventors: Kevin T. Foley, Germantown, TN (US);
Richard D. Bucholz, St. Louis, MO (US); Kurt R. Smith, Boulder, CO (US)

(*) Notice: Subject to any disclaimer, the term of this patent is extended or adjusted under 35 U.S.C. 154(b) by 1593 days.

This patent is subject to a terminal disclaimer.

(21) Appl. No.: 11/311,740

(22) Filed: Dec. 19, 2005

(65) Prior Publication Data

US 2006/0122483 A1    Jun. 8, 2006

Related U.S. Application Data

(63) Continuation of application No. 10/198,324, filed on Jul. 18, 2002, now Pat. No. 6,978,166, which is a continuation of application No. 09/398,313, filed on Sep. 20, 1999, now Pat. No. 6,434,415, which is a continuation of application No. 08/931,654, filed on Sep. 16, 1997, now Pat. No. 6,347,240, which is a continuation of application No. 08/319,615, filed on Oct. 7, 1994, now abandoned.

(51) Int. Cl.
*A61B 6/00* (2006.01)
(52) U.S. Cl. ........ 600/425; 600/426; 600/427; 600/429; 606/130
(58) Field of Classification Search .................. 600/407, 600/410, 411, 414, 417, 425–427, 429, 437, 600/439; 606/130; 378/54, 205
See application file for complete search history.

(56) References Cited

U.S. PATENT DOCUMENTS

| 3,821,469 A | 6/1974 | Whetstone et al. |
| 3,868,565 A | 2/1975 | Kuipers |
| 3,963,028 A | 6/1976 | Cooley et al. |
| 3,983,474 A | 9/1976 | Kuipers |
| 4,058,114 A | 11/1977 | Soldner |
| 4,068,156 A | 1/1978 | Johnson et al. |
| 4,117,337 A | 9/1978 | Staats |
| 4,182,312 A | 1/1980 | Mushabac |

(Continued)

FOREIGN PATENT DOCUMENTS

DE    2534516    2/1976

(Continued)

OTHER PUBLICATIONS

Adams et al., "Aide Au Reperage Tridimensionnel Pour La Chirurgie De La Base Du Crane," Innov. Tech. Biol. Med., vol. 13, No. 4, pp. 409-424, 1992.

(Continued)

*Primary Examiner* — Ruth S Smith
(74) *Attorney, Agent, or Firm* — Senniger Powers LLP

(57) ABSTRACT

A system for use during a medical or surgical procedure on a body. The system modifies a reference image data set according to a density image of a body element during a procedure, generates a displaced image data set representing the position and geometry of the body element during the procedure, and compares the density image of the body element during the procedure to the reference image of the body element. The system also includes a display utilizing the displaced image data set generated by the processor to illustrate the position and geometry of the body element during the procedure. Methods relating to the system are also disclosed.

40 Claims, 11 Drawing Sheets

U.S. PATENT DOCUMENTS

| | | |
|---|---|---|
| 4,209,254 A | 6/1980 | Reymond |
| 4,259,725 A | 3/1981 | Andrews et al. |
| 4,341,220 A | 7/1982 | Perry |
| 4,358,856 A | 11/1982 | Stivender et al. |
| 4,368,556 A | 1/1983 | Wanner et al. |
| 4,396,945 A | 8/1983 | DiMatteo et al. |
| 4,398,540 A | 8/1983 | Takemura et al. |
| 4,407,298 A | 10/1983 | Lentz et al. |
| 4,419,012 A | 12/1983 | Stephenson et al. |
| 4,457,311 A | 7/1984 | Sorenson et al. |
| 4,465,069 A | 8/1984 | Barbler et al. |
| 4,473,074 A | 9/1984 | Vassiliadis |
| 4,506,676 A | 3/1985 | Duska |
| 4,543,959 A | 10/1985 | Sepponen |
| 4,571,834 A | 2/1986 | Fraser et al. |
| 4,583,538 A | 4/1986 | Onik et al. |
| 4,585,350 A | 4/1986 | Pryer et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Shelden et al. |
| 4,649,504 A | 3/1987 | Krouglicof et al. |
| 4,651,732 A | 3/1987 | Frederick |
| 4,659,971 A | 4/1987 | Suzuki et al. |
| 4,660,970 A | 4/1987 | Ferrano |
| 4,672,306 A | 6/1987 | Thong |
| 4,673,352 A | 6/1987 | Hansen |
| 4,674,057 A | 6/1987 | Caughman et al. |
| D291,246 S | 8/1987 | Lower |
| 4,686,997 A | 8/1987 | Oloff et al. |
| 4,698,777 A | 10/1987 | Toyoda et al. |
| 4,701,047 A | 10/1987 | Eibert et al. |
| 4,701,049 A | 10/1987 | Beckman et al. |
| 4,701,407 A | 10/1987 | Appel |
| 4,705,395 A | 11/1987 | Hageniers |
| 4,705,401 A | 11/1987 | Addleman |
| 4,706,665 A | 11/1987 | Gouda |
| 4,709,156 A | 11/1987 | Murphy et al. |
| 4,721,384 A | 1/1988 | Dietrich et al. |
| 4,721,388 A | 1/1988 | Takagi et al. |
| 4,722,056 A | 1/1988 | Roberts et al. |
| 4,723,544 A | 2/1988 | Moore et al. |
| 4,727,565 A | 2/1988 | Ericson |
| 4,733,661 A | 3/1988 | Palestrant |
| 4,733,662 A | 3/1988 | DeSatnick et al. |
| 4,733,969 A | 3/1988 | Case et al. |
| 4,737,032 A | 4/1988 | Addleman et al. |
| 4,737,921 A | 4/1988 | Goldwasser et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Bartlett et al. |
| 4,753,528 A | 6/1988 | Hines |
| 4,761,072 A | 8/1988 | Pryor |
| 4,762,016 A | 8/1988 | Stoughton et al. |
| 4,764,015 A | 8/1988 | Bieringer et al. |
| 4,764,016 A | 8/1988 | Johansson |
| 4,767,934 A | 8/1988 | Stauffer |
| 4,771,787 A | 9/1988 | Wurster et al. |
| 4,775,235 A | 10/1988 | Hecker et al. |
| 4,776,749 A | 10/1988 | Wanzenberg et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,803,645 A | 2/1989 | Ohtomo et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,837,669 A | 6/1989 | Tharp et al. |
| 4,841,967 A | 6/1989 | Chang et al. |
| 4,875,478 A | 10/1989 | Chen |
| 4,896,673 A | 1/1990 | Rose et al. |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,955,891 A | 9/1990 | Carol |
| 4,961,422 A | 10/1990 | Marchosky |
| 4,982,188 A | 1/1991 | Fodale et al. |
| 4,991,579 A | 2/1991 | Allen |
| 5,005,142 A | 4/1991 | Lipchak et al. |
| 5,016,639 A | 5/1991 | Allen |
| 5,017,139 A | 5/1991 | Mushabac |
| 5,027,810 A | 7/1991 | Patureau et al. |
| 5,039,867 A | 8/1991 | Nishihara et al. |
| 5,040,012 A | 8/1991 | Eklund et al. |
| 5,047,036 A | 9/1991 | Koutrouvelis |
| 5,050,608 A | 9/1991 | Watanabe et al. |
| 5,059,789 A | 10/1991 | Salcudean et al. |
| 5,078,140 A | 1/1992 | Kwoh |
| 5,078,142 A | 1/1992 | Siczek et al. |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,166,876 A | 11/1992 | Cline et al. |
| 5,178,164 A | 1/1993 | Allen |
| 5,186,174 A | 2/1993 | Schlöndorff et al. |
| 5,193,106 A | 3/1993 | DeSena |
| 5,197,476 A | 3/1993 | Nowacki et al. |
| 5,207,223 A | 5/1993 | Adler |
| 5,211,164 A | 5/1993 | Allen |
| 5,222,499 A | 6/1993 | Allen et al. |
| 5,224,049 A | 6/1993 | Mushabac |
| 5,230,338 A | 7/1993 | Allen et al. |
| 5,249,581 A | 10/1993 | Horbal et al. |
| 5,251,127 A | 10/1993 | Raab |
| 5,257,998 A | 11/1993 | Ota et al. |
| 5,261,404 A | 11/1993 | Mick et al. |
| 5,279,309 A | 1/1994 | Taylor et al. |
| 5,291,889 A | 3/1994 | Kenet et al. |
| 5,295,200 A | 3/1994 | Boyer |
| 5,295,483 A | 3/1994 | Nowacki et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| D349,573 S | 8/1994 | Bookwalter et al. |
| 5,355,129 A | 10/1994 | Baumann |
| 5,357,953 A | 10/1994 | Merrick et al. |
| 5,359,417 A | 10/1994 | Müller et al. |
| 5,368,030 A | 11/1994 | Zinreich et al. |
| D353,668 S | 12/1994 | Banks et al. |
| 5,371,778 A | 12/1994 | Yanof et al. |
| 5,383,454 A | 1/1995 | Bucholz |
| 5,389,101 A | 2/1995 | Heilbrun et al. |
| 5,391,199 A | 2/1995 | Ben-Haim |
| 5,398,684 A | 3/1995 | Hardy |
| 5,399,146 A | 3/1995 | Nowacki et al. |
| 5,399,951 A | 3/1995 | Lavallee et al. |
| D357,534 S | 4/1995 | Hayes |
| D359,557 S | 6/1995 | Hayes |
| 5,443,489 A | 8/1995 | Ben-Haim |
| 5,447,154 A | 9/1995 | Cinquin et al. |
| 5,480,422 A | 1/1996 | Ben-Haim |
| 5,483,961 A | 1/1996 | Kelly et al. |
| 5,490,196 A | 2/1996 | Rudich et al. |
| 5,494,034 A | 2/1996 | Schlondorff et al. |
| 5,515,160 A | 5/1996 | Schulz et al. |
| 5,517,990 A | 5/1996 | Kalfas et al. |
| 5,526,576 A | 6/1996 | Fuchs et al. |

| | | | |
|---|---|---|---|
| 5,531,227 | A | 7/1996 | Schneider |
| 5,531,520 | A | 7/1996 | Grimson et al. |
| 5,546,951 | A | 8/1996 | Ben-Haim |
| 5,551,429 | A | 9/1996 | Fitzpatrick et al. |
| 5,558,091 | A | 9/1996 | Acker et al. |
| 5,568,809 | A | 10/1996 | Ben-Haim |
| 5,603,318 | A | 2/1997 | Heilbrun et al. |
| 5,617,857 | A | 4/1997 | Chader et al. |
| 5,622,170 | A | 4/1997 | Schulz |
| 5,638,819 | A | 6/1997 | Manwaring et al. |
| 5,647,361 | A | 7/1997 | Damadian |
| 5,649,936 | A | 7/1997 | Real |
| 5,662,111 | A | 9/1997 | Cosman |
| 5,676,673 | A | 10/1997 | Ferre et al. |
| 5,682,886 | A | 11/1997 | Delp et al. |
| 5,728,106 | A | 3/1998 | Misko et al. |
| 5,732,703 | A | 3/1998 | Kalfas et al. |
| 5,769,861 | A | 6/1998 | Vilsmeier |
| 5,776,064 | A | 7/1998 | Kalfas et al. |
| 5,792,147 | A | 8/1998 | Evans et al. |
| 5,794,356 | A | 8/1998 | Raab |
| 5,848,967 | A | 12/1998 | Cosman |
| 6,006,126 | A | 12/1999 | Cosman |
| 6,236,875 | B1 | 5/2001 | Bucholz et al. |
| 6,347,240 | B1 | 2/2002 | Foley et al. |
| 6,434,415 | B1 | 8/2002 | Foley et al. |
| 6,978,166 | B2 * | 12/2005 | Foley et al. .............. 600/425 |

FOREIGN PATENT DOCUMENTS

| | | |
|---|---|---|
| DE | 2852949 | 6/1980 |
| DE | 3205085 | 9/1982 |
| DE | 3508730 | 9/1986 |
| DE | 8701668 | 5/1987 |
| DE | 3838011 A1 | 7/1989 |
| DE | 3717871 C2 | 11/1989 |
| DE | 3904595 C1 | 4/1990 |
| DE | 3205915 | 9/1993 |
| DE | 4233978 C1 | 4/1994 |
| DE | 4432890 | 3/1996 |
| EP | 0 018 166 | 4/1980 |
| EP | 0 062 941 | 10/1982 |
| EP | 0 155 857 | 1/1985 |
| EP | 0 207 452 | 1/1987 |
| EP | 0 322 363 | 6/1989 |
| EP | 0 427 358 | 10/1990 |
| EP | 0 456 103 | 5/1991 |
| EP | 0 469 966 | 2/1992 |
| EP | 0 359 773 | 10/1993 |
| EP | 0 581 704 | 2/1994 |
| EP | 0 603 089 | 6/1994 |
| EP | 0 501 993 | 5/1996 |
| EP | 0 326 768 | 12/1998 |
| FR | 2417970 | 10/1979 |
| GB | 2094590 | 2/1982 |
| JP | 62-000327 | 1/1987 |
| JP | 62-74385 | 3/1997 |
| WO | WO 88/09151 | 12/1988 |
| WO | WO 90/05494 | 5/1990 |
| WO | WO 91/04711 | 4/1991 |
| WO | WO 91/07726 | 5/1991 |
| WO | WO 92/00702 | 1/1992 |
| WO | WO 92/06645 | 4/1992 |
| WO | WO 93/10710 | 6/1993 |
| WO | WO 93/02052 | 10/1993 |
| WO | WO 94/06352 | 3/1994 |
| WO | WO 94/23647 | 10/1994 |
| WO | WO 94/24933 | 11/1994 |
| WO | WO 95/11624 | 5/1995 |
| WO | WO 96/11624 | 4/1996 |

OTHER PUBLICATIONS

Adams et al., "Medical Imaging: Computer-Assisted Surgery," IEEE Computer Graphics & Applications, May 1990, pp. 43-51.

Afshar et al., "A Three-Dimensional Reconstruction of the Human Brain Stem," J. Neurosurg., vol. 57, No. 4, Oct. 1982, pp. 491-495.

Apuzzo et al., "Computed Tomographic Guidance Stereotaxis in the Management of Intracranial Mass Lesions," Neurosurgery, vol. 12, No. 3, 1983, pp. 277-285.

Arun et al., "Transactions on Pattern Analysis and Machine Intelligence," IEEE, vol. PAMI-9, No. 5, 1987, pp. 698-770.

Awwad et al., "Post-Traumatic Spinal Synovial Cyst with Spondylolysis CT Features," Journal of Computer Assisted Tomography, vol. 13, No. 2, Mar./Apr. 1989, pp. 334-337.

Awwad et al., "MR Imaging of Lumbar Juxtaarticular Cysts," Journal of Computer Assisted Tomography, vol. 14, No. 3, May/Jun. 1990, pp. 415-417.

Bajcsy et al., "Computerized Anatomy Atlas of the Human Brain," Proceedings of the Second Annual Conference & Exhibition of the National Computer Graphics Association, Inc., 1981, pp. 435-441.

Balter et al., "Correlation of Projection Radiographs in Radiation Therapy Using Open Curve Segments and Points," Med. Phys. 19(2), Mar./Apr. 1992, pp. 329-334.

Batnitzky et al., "Three-Dimensional Computer Reconstructions of Brain Lesions from Surface Contours Provided by Computed Tomography: A Prospectus," Neurosurgery, vol. 11, No. 1, Jul. 1982, pp. 73-84.

Benzel et al., "Magnetic Source Imaging: A Review of the Magnes System of Biomagnetic Technologies Incorporated," Neurosurgery, vol. 33, No. 2, Aug. 1993, pp. 252-259.

Bergström et al., "Stereotaxic Computed Tomography," Am. J. Roentgenol, vol. 127, pp. 167-170, 1976.

Birg et al., "A Computer Programme System for Stereotactic Neurosurgery," Acta Neurochirurgica Suppl., 24, 1977, pp. 99-108.

Boëthius et al., "Stereotaxic Computerized Tomography with a GE 8800 Scanner," J. Neurosurg., vol. 52, Jun. 1980, pp. 794-800.

Boëthius et al., "Stereotactic Biopsies and Computer Tomography in Gliomas," Acta Neurochirurgica, vol. 40, Fasc. 3-4, 1978, pp. 223-232.

Brown, "A Computerized Tomography-Computer Graphics Approach to Stereotaxic Localization," J. Neurosurg, vol. 50, No. 6, 1979, pp. 715-720.

Brown, "A Stereotactic Head Frame for Use with CT Body Scanners," Inv. Radiol, vol. 14, No. 4, Jul. 1979, pp. 300-304.

Bucholz et al., "Intraoperative Ultrasonic Brain Shift Monitor and Analysis," St. Louis University Hospital, 1997.

Bucholz, "The Central Sulcus and Surgical Planning," AJNR, vol. 14, Jul./Aug. 1993, pp. 926-927.

Bucholz et al., "Halo Vest Versus Spinal Fusion for Cervical Injury: Evidence from an Outcome Study," J. Neurosurg., vol. 70, No. 6, Jun. 1989, pp. 884-892.

Bucholz, "Declaration of Richard D. Bucholz," pp. 1-4, with attached Exhibits A (pp. 1-29) and B (pp. 1-2), Dec. 2-3, 1997.

Bucholz et al., "Use of an Intraoperative Optical Digitizer in a System for Free-Hand Stereotactic Surgery," Poster #1120, Scientific Program, 1992 Annual Meeting, American Association of Neurological Surgeons, Apr. 11-16, 1992, pp. 284-285, San Francisco, California.

Bucholz et al., "Variables Affecting the Accuracy of Stereotactic Localization Using Computerized Tomography," J. Neurosurg., vol. 79, No. 1993, pp. 667-673.

Bucholz et al., "Intraoperative Localization Using a Three Dimensional Optical Digitizer," Proceedings of Clinical Applications of Modern Imaging Technology, SPIE, vol. 1894, The International Soceity of Optical Engineering, Jan. 17-19, 1993, pp. 312-322.

Bucholz et al., "Image-Guided Surgical Techniques for Infections and Trauma of the Central Nervous System," Neurosurgery Clinics of North America, vol. 7, No. 2, pp. 187-200, Apr. 1996.

Bullard et al., "C.T.-Guided Stereotactic Biopsies Using a Modified Frame and Gildenberg Techniques," Neurology, Neurosurgery, and Psychiatry, vol. 47, 1984, pp. 590-595.

BYTE Magazine, "3-D Digitizer Captures the World," 1990, p. 43.

Champleboux et al., "Accurate Calibration of Cameras and Range Imaging Sensors: the NPBS Method," IEEE Conference on Robotics and Automation, 1992, 6 pages.

Champleboux, "Utilisation De Fonctions Splines Pour La Mise Au Poit d'Un Capteur Tridimension Sans Contact," These, Docteur de L'Univerite' Joseph Fourie Grenoble, Jul. 1991.

Cinquin et al., "Computer Assisted Medical Interventions, The 1st Workshop on Domestic Robotics—The 2nd Workshop on Medical & Healthcare Robotics," Sep. 5-7, 1989, pp. 63-65.

Cinquin et al., "IGOR: Image Guided Operating Robot, Methodology, Applications," IEEE EMBS, Paris, 1992, pp. 1-2.

Clarysse et al., "A Computer-Assisted System for 3-D Frameless Localization in Stereotaxic MRI," IEEE TOMA, vol. 10, No. 4, pp. 523-529, Dec. 1991.
Dever et al., "OR Role Seen for 3-D Imaging," Radiology Today, Feb. 1991, 2 pages.
Foley et al., "Image-Guided Intraoperative Spinal Localization," Intraoperative Neuroprotection, Chapter 19, 1996, pp. 325-340.
Friets et al., "A Frameless Stereotaxic Operating Microscope for Neurosurgery," IEEE Transactions on Biomedical Engineering, vol. 36, No. 6, Jun. 1989, pp. 608, 613-617.
Gallen et al., "Intracranial Neurosurgery Guided by Functional Imaging," Surg. Neurol., vol. 42, pp. 523-530, Jan. 3, 1994.
Galloway, Jr. et al., "Interactive Image-Guided Neurosurgery," IEEE Transactions on Biomedical Engineering, vol. 39, No. 12, Dec. 1992, pp. 1226-1231.
Gildenberg et al., "Calculation of Stereotactic Coordinates from the Computed Tomographic Scan," Neurosurgery, vol. 10, No. 5, May 1982, pp. 580-586.
Glaser et al., "The Image-Combining Computer Microscope—an Interactive Instrument for Morphometry of the Nervous System," Journal of Neuroscience Methods, vol. 8, 1983, pp. 17-32.
Gleason et al., "Stereotactic Localization (with Computerized Tomographic Scanning), Biopsy, and Radiofrequency Treatment of Deep Brain Lesions," Neurosurgery, vol. 2, No. 3, 1978, pp. 217-222.
Golfinos et al., "Clinical Use of a Frameless Stereotaxic Arm: results of 325 cases," J. Neurosurg., vol. 83, No. 3, pp. 197-205, Aug. 1995.
Gomez et al., "Transcranial Doppler Ultrasound Following Closed Head Injury: Vasospasm or Vasoparalysis?," Surg. Neurol., vol. 35, No. 1, Jan. 1991, pp. 30-35.
Gonzalez et al., "Digital Image Fundamentals," Digital Imaging Processing Second Edition, Addison-Wesley Publishing Company, 1987, pp. 52-54.
Gouda et al., "New Frame for Stereotaxic Surgery," J. Neurosurg., vol. 53, Aug. 1980, pp. 256-259.
Greitz et al., "Head Fixation System for Integration of Radiodiagnostic and Therapeutic Procedures," Neuroradiology, vol. 19, No. 1, 1980, pp. 1-6.
Hahn et al., "Needle Biopsy of Intracranial Lesions Guided by Computerized Tomography," Neurosurgery, vol. 5, No. 1, 1979, pp. 11-15.
Hanson et al., "Robots Roll into Operating Room," Insight, Apr. 8, 1991, pp. 44-45.
Hatch, "Reference-Display System for the Integration of CT Scanning and the Operating Microscope," Proceedings of the Eleventh Annual Northeast Bioengineering Conference, Mar. 14-15, 1985, IEEE 1985, pp. 252-254; Trustees of Dartmouth College, Oct. 1984, entire thesis.
Heilbrun, "Computed Tomography-Guided Stereotactic Systems," Clinical Neurosurgery, 1983, pp. 564-580.
Heilbrun et al., "Preliminary Experience with a Brown-Roberts-Wells (BRW) Computerized Tomography Stereotaxic Guidance System," J. Neurosurg., vol. 59, Aug. 1983, pp. 217-222.
Henderson et al., "An Accurate and Ergonomic Method of Registration for Image-Guided Neurosurgery," Computerized Medical Imaging and Graphics, vol. 18, No. 4, pp. 273-277, 1994.
Hinck et al., "A Precise Technique for Craniotomy Localization Using Computerized Tomography," J. Neurosurg., vol. 54, No. 3, Mar. 1981, pp. 416-418.
Hoerenz, "The Operating Microscope, I., Optical Principles, Illumination Systems, and Support Systems," Journal of Microsurgery, vol. 2, No. 5, Mar.-Apr. 1980, pp. 364-369.
Holman et al, "Computer-Assisted SUperimposition of Magnetic Resonance and High-Resolution Technetium-99-m-HMPAO and Thallium-201 SPECT Images of the Brain," The Journal of Nuclear Medicine, vol. 32, No. 8, Aug. 1991, pp. 1478-1484.
Horner et al., "A Comparison of CT-Stereotaxic Brain Biopsy Techniques," Investigative Radiology, vol. 19, Sep.-Oct. 1984, pp. 367-373.
Hounsfield, "Computerized Transverse Axial Scanning (Tomography): Part 1, Description of System," British Journal of Radiology, vol. 46, 1973, pp. 1016-1022.
Jacques et al., "Computerized Three-Dimensional Stereotaxic Removal of Small Central Nervous System Lesions in Patients," J. Neurosurg., vol. 53, No. 6, Dec. 1980, pp. 816-820.
Jacques et al., "A Computerized Microstereotactic Method to Approach, 3-Dimensionally Reconstruct, Remove and Adjuvantly Treat Small CNS Lesions," Appl. Neurophysiology, vol. 43, pp. 176-182, 1980.
Kato et al., "A Frameless Armless Navigational System for Computer Assisted Neurosurgery," J. Neurosurg., vol. 74, pp. 845-849, May 1991.
Kaufman, "New Head-Positioning System for Use with Computed Tomographic Scanning," Neurosurgery, vol. 7, No. 2, Aug. 1980, pp. 147-149.
Kelly et al., "A Microstereotactic Approach to Deep-Seated Arteriovenous Malformations," Surgical Neurology, vol. 17, No. 4, Apr. 1982, pp. 260-262.
Kelly et al., "Computer-Assisted Stereotaxic Laser Resection of Intra-Axial Brain Neoplasma," J. Neurosurg., vol. 64, Mar. 1986, pp. 427-439.
Kelly et al., "A Stereotactic Approach to Deep-Seated Central Nervous System Neoplasms Using the Carbon Dioxide Laser," Surgical Neurology, vol. 15, No. 5, May 1981, pp. 331-334.
Kelly et al., "Stereotactic CT Scanning for the Biopsy of Intracranial Lesions and Functional Neurosurgery," Applied Neurophysiology, vol. 46, Dec. 1983, pp. 193-199.
Kelly et al., "Precision Resection of Intra-Axial CNS Lesions by CT-Based Stereotactic Craniotomy and Computer Monitored $CO_2$ Laser," Acta Neurochirurgica, vol. 68, Fasc. 1-2, 1983, pp. 1-9.
Kelly, "Instrumentation, Tecnique and Technology," Neurosurgery, vol. 37, No. 2, pp. 348-350, Aug. 1995.
Klimek et al., "Long-Term Experience with Different Types of Localization Systems in Skull-Base Surgery," Ear, Nose and Throat Surgery, vol. 51, pp. 635-638, 1992.
Kondziolka et al., "Guided Neurosurgery Using the ISG Viewing Wand," Contemporary Neurosurgery, vol. 17, No. 8, pp. 1-6, 1995.
Kosugi et al., "An Articulated Neurosurgical Navigation System Using MRI and CT Images," IEEE Transaction on Biomedical Engineering, vol. 35, No. 2, Feb. 1988, pp. 147-152.
Krybus et al., "Navigation Support for Surgery by Means of Optical Position Detection,"Proceedings of CAR 1991, pp. 362-366.
Laitinen, "Trigeminus Stereoguide: An Instrument for Stereotactic Approach Through the Foramen Ovale and Foramen Jugulare," Surg. Neurol., vol. 22, pp. 519-525, 1984.
Lavallee et al., "Computer Assisted Interventionist Imaging: The Instance of Stereotactic Brain Surgery," Medinfo, pp. 613-617, 1989.
Lavallee et al., "Computer Assisted Medial Interventions," NATO ASI Series, vol. F60, pp. 301-312, 1990.
Lavallee et al., "Matching 3-D Smooth Surfaces with Their 2-D Projections Using 3-D Distance Maps," SPIE, vol. 1570, Geometric Methods in Computer Vision, 1991, pp. 322-336.
Lavallee, "A New System for Computer Assisted Neurosurgery," IEEE Engineering in Medicine & Biology Society 11th Annual International Conference, 2 pages, 1989.
Lavallee et al., "Ponction Assistee Par Ordinateur" ("Computer Assisted Puncture"), afcet INRIA, pp. 439-449, Nov. 16-20, 1987.
Lavallee et al., "Computer Assisted Driving of a Needle into the Brain," Computer Assisted Radiology Magazine, pp. 416-420, 1989.
Lavallee et al., "Matching of Medical Images for Computed and Robot Assisted Surgery," 1991.
Lavallee et al., "Vi Adaptation de la Methodologie: A Quelques Applications Clinques," Lere Partie: Methodologie des GMCAO, Chapter VI, undated, pp. 133-148.
Leksell et al., "Stereotaxis and Tomography, a Technical Note," Acta Neurochirurgica, vol. 52, Fasc 1-2, 1980, pp. 1-7.
Levin et al., "Multimodality 3-D View of the Brain Created from MRI and PET Scans," SMRI 1989: Seventh Annual Meeting Program and Abstracts, vol. 7, Supplement 1, p. 89.
Levin et al., "The Brain: Integrated Three-Dimensional Display of MR and PET Images," Radiology, 1989, vol. 172, No. 3, pp. 783-789.
Levinthal et al., "Technique for Accurate Localization with the CT Scanner," Bulletin of the Los Angeles Neurological Societies, vol. 41, No. 1, Jan. 1976, pp. 6-8.
Levy et al., "Heads-up Intraopertive Endoscopic Imaging: A Prospective Evaluation of Techniques and Limitations," Neurosurgery, vol. 40, No. 3, pp. 526-529, Mar. 1997.

Lunsford, "Innovations in Stereotactic Technique Coupled with Computerized Tomography," Contemporary Neurosurgery, 1982, pp. 1-6.

MacKay et al., "Computer Tomography-Directed Stereotaxy for Biopsy and Interstitial Irradiation of Brain Tumors: Technical Note," Neurosurgery, vol. 11, No. 1, 1982, pp. 38-42.

Mallet et al., "Post-Laminectomy Cervical-Thoracic Kyphosis in a Patient with Von Recklinghausen's Disease," Spinal Frontiers, vol. 3, Issue 1, Apr. 1996.

Maroon et al., "Intracranial Biopsy Assisted by Computerized Tomography," J. Neurosurg., vol. 46, No. 6, Jun. 1977, pp. 740-744.

Mazier et al., "Computer Assisted Interventionist Imaging: Application to the Vertebral Column Surgery," IEEE, vol. 12, No. 1, 1990, pp. 430-431.

Mazier et al., "Computer Assisted Vertebral Column Surgery: Application to the Spinal Pedicle Fixation," Innov. Techn. Biol. Med., vol. 11, No. 5, 1990, pp. 559-565.

Mazier et al., "Chirurgie De La Colonne Vertebrate Assiste Par Ordinateur: Application Au Vissage Pediculaire," Innov. Tech. Biol. Med., vol. 11, No. 5, pp. 559-566, 1990.

Mesqui et al., "Real-Time Noninvasive Recording and Three-Dimensional Display of the Functional Movements of an Arbitrary Mandible Point," SPIE Biostereometrics '85, vol. 602, pp. 77-84, Dec. 3-6, 1985.

Moran et al., "Central Nervous System Lesions Biopsied or Treated by CT-Guided Needle Placement," Radiology, vol. 131, No. 3, Jun. 1979, pp. 681-686.

Mösges et al., "A New Imaging Method for Intraoperative Therapy Control in Skull-Base Surgery," Neurosurg., Rev. 11, pp. 245-247, 1988.

Mundinger et al., "Computer-Assisted Stereotactic Brain Operations by Means Including Computerized Axial Tomography," Applied Neurophysiology, vol. 41, No. 1-4, 1978, pp. 169-182.

Mundlinger et al., "Treatment of Small Cerebral Gliomas with CT-Aided Stereotaxic Curietherapy," Neuroradiology, vol. 16, 1978, pp. 564-567.

Norman et al., "Localization with the EMI Scanner," The American Journal of Roentgenology, Radium Therapy and Nuclear Medicine, vol. 125, No. 4, Dec. 1975, pp. 961-964.

Ohbuchi et al., "Incremental Volume Reconstruction and Rendering for 3D Ultrasound Imaging," Visualization in Biomedical Computing, SPIE, vol. 1808, pp. 312-323, 1992.

O'Leary et al., "Localization of Vertex Lesions Seen on CT Scan," J. Neurosurg., vol. 49, No. 1, Jul. 1978, pp. 71-74.

Olivier et al., "Frameless Stereotaxy for Surgery of the Epilepsies: Preliminary Experience," J. Neurosurg., vol. 81, No. 4, pp. 628-633, Oct. 1994.

Patil, "Computed Tomography Plane of the Target Approach in Computed Tomographic Stereotaxis," Neurosurgery, vol. 15, No. 3, Sep. 1984, pp. 410-414.

Paul et al., "Development of a Surgical Robot for Cementless Total Hip Arthroplasty," Clinical Orthopaedics, No. 285, Dec. 1992, pp. 57-66.

Pelizzari et al., "Accurate Three-Dimensional Registration of CT, PET and/or MR Images of the Brain," Journal of Computer Assisted Tomography, 13(1), Jan./Feb. 1989, pp. 20-26.

Pelizzari et al., "3D Patient/Image Registration: Application to Radiation Treatment Planning," Medical Physics, vol. 18, No. 3, May/Jun. 1991, p. 612.

Pelizzari et al., "Three Dimensional Correlation of PET, CT and MRI Images," The Journal of Nuclear Medicine, Abstract Book, 34th Annual Meeting, vol. 28, No. 4, Poster Session No. 528, 1987, p. 682.

Pelizzari et al., "Interactive 3D Patient-Image Registration," Lecture Notes in Computer Science 12th International Conference, Information Procession in Medical Imaging, Springer-Verlag, Wye, UK, 1991, pp. 132-141.

Penn et al., "Stereotactic Surgery with Image Processing of Computerized Tomographics Scans," Neurosurgery, vol. 3, No. 2, Sep./Oct. 1978, pp. 157-163.

Perry et al., "Computed Tomography-Guided Stereotactic Surgery: Conception and Development of a New Stereotactic Methodology," Neurosurgery, vol. 7, No. 4, Oct. 1980, pp. 376-381.

Picard et al., "The First Human Stereotaxic Apparatus," J. Neurosurg., vol. 59, Oct. 1983, pp. 673-676.

Piskun et al., "A Simplified Method of CT Assisted Localization and Biopsy of Intracranial Lesions," Surgical Neurology, vol. 11, Jun. 1979, pp. 413-417.

Pixsys, Inc., "SACDAC User's Guide, Version 2e," Mar. 1989, pp. 0-1 through 5-3.

Pixsys, Inc., "Design Aide," Mar. 1989, 5 unnumbered pages.

Pixsys, Inc., "Pixsys: 3-D Digitzing Accessories," Aug. 1989, 6 unnumbered pages.

Pixsys, Inc., "Offset Probe for Science Accessories' GP-8-3D Digitizer," Dec. 1987, one page.

Pixsys, Inc., "Real-Time Image-Guided Surgery and Planning, FlashPoint 3D Localizer," Investigational Device Brochure, 3 pages, unnumbered, undated.

Pixsys, Inc., "Alignment Procedure for the Pixsys Two-Emitter Offset Probe for the SAC GP-8-3d Sonice Digitizer," undate, 3 unnumered pages.

Reinhardt et al., "CT-Guided 'Real Time' Stereotaxy," Acta Neurochirurgica Suppl. 46, 1989, pp. 107-108.

Reinhardt et al., "A Computer Assisted Device for the Intra Operate CT-Correlated Localization of Brain Tumors," 1988, Eur. Surg. Res., vol. 20, pp. 52-58.

Reinhardt et al., "Mikrochirugicshe Entfurnung tifliegender Gefaßmißbildungen mit Hilfe der Sonar-Stereometrie," Ultraschall in Med. 12, 1991, pp. 80-84.

Reinhardt, "Surgery of Brain Neoplasms Using 32-P Tumor Marker," Acta Neurochir, vol. 97, pp. 89-94, 1989.

Reinhardt et al., "Neuronavigation: A Ten-Year Review," Neurosurgery, vol. 23, pp. 329-341, 1992.

Reinhardt, "Sonic Stereometry in Microsurgical Procedures for Deep-Seated Brain Tumors and Vascular Malformations," Neurosurgery, vol. 32, No. 1, Jan. 1993, pp. 51-57.

Reinhardt et al., "Interactive Sonar-Operated Device for Stereotactic and Open Surgery," Stereotac. Funct. Neurosurg., 1990, vols. 54 and 55, pp. 393-397.

Roberts et al., "A Frameless Stereotaxic Integration of Computerized Tomographic Imaging and the Operating Microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, Jan. 1980, pp. 172-173.

SAC Science Accessories Corporation, "Model GP-8 Sonic Digitizer, Mark II Sonic Digitizer (Model GP-7 Grafbar), 3-Dimensional Sonic Digitizer (Model GP-8-3D)," Technical Bulletin, 6 pages, unnumbered, undated.

Sautot et al., "Computer Assisted Spine Surgery: A First Step Toward Clinical Application in Orthopaedics," 14th IEEE EMBS, pp. 1071-1072, 1992.

Scarabin et al., "Stereotaxic Exploration in 200 SUpratentorial Braintumors," Neuroradiology, vol. 16, Jun. 4-10, 1978, pp. 591-593.

Shelden et al., "Development of a Computerized Microstereotaxic Method for Localization and Removal of Minute CNS Lesions Under Direct 3-D Vision," J. Neurosurg., vol. 52, Jan. 1980, pp. 21-27.

Shiu et al., "Finding the Mounting Position of a Sensor by Solving a Homogeneous Transform Equation of Form AX=XB," IEEE, vol. 3, 1987, pp. 1666-1671.

Smith et al., "The Neurostation TM—Highly Accurate, Minimally Invasive Solution to Frameless Stereotactic Neurosurgery," Computered Medical Imaging and Graphics, vol. 18, No. 4, 1994, pp. 247-256.

Smith et al., "Multimodality Image Analysis and Display Methods for Improved Tumor Localization in Stereotactic Neurosurgery," Annual Conference for the IEEE Engineering in Medicine and Biology Society, vol. 13, No. 1, 1991, p. 210.

Smith et al., "Computer Methods for Improved Diagnostic Image Display Applied to Stereotactic Neurosurgery," Automedica, vol. 14, 1992, pp. 371-382.

Spencer et al., "Unilateral Transplantation of Human Fetal Mesancephalic Tissue into the Caudate Nucleus of Patients with Parkinson's Disease," The New England Journal of Medicine, vol. 327, No. 22, Nov. 26, 1992, pp. 1541-1548.

Valentino et al., "Three-Dimensional Visualization of Human Brain Structure-Function Relationships," The Journal of Nuclear Medicine, 1989, Posterboard 1136, vol. 30, No. 10, p. 1747.

Van Buren et al., "A Multipurpose CT-Guided Stereotactic Instrument of Simple Design," Applied Neurophysiology, Jan.-Aug. 1983, pp. 211-216.

Watanabe et al., "Three Dimensional Digitizer (Neuronavigator): New Equipment for Computed Tomography—Guided Stereotaxic Surgery," 27 Surg. Neurol., 1987, pp. 543-547.

Watanabe et al., "Neuronavigator," Igaku-no-Ayumi, vol. 137, No. 6, May 10, 1986, pp. 1-4.

Yeates et al., "Simplified and Accurate CT-Guided Needle Biopsy of Central Nervous System Lesions," Journal of Neurosurgery, vol. 57, No. 3, Sep. 1982, pp. 390-393.

Yosugi et al., "An Articulated Neurosurgical Navigation System Using MRI and CT Images," Feb. 1988, pp. 147-152.

* cited by examiner

POSITION IN SURGERY
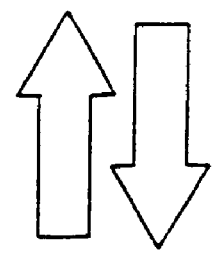
REGISTRATION
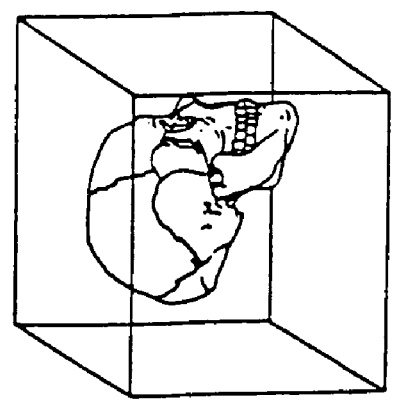
PRE-SURGICAL SCANS (IMAGE DATASET)
FIG. 1
PRIOR ART

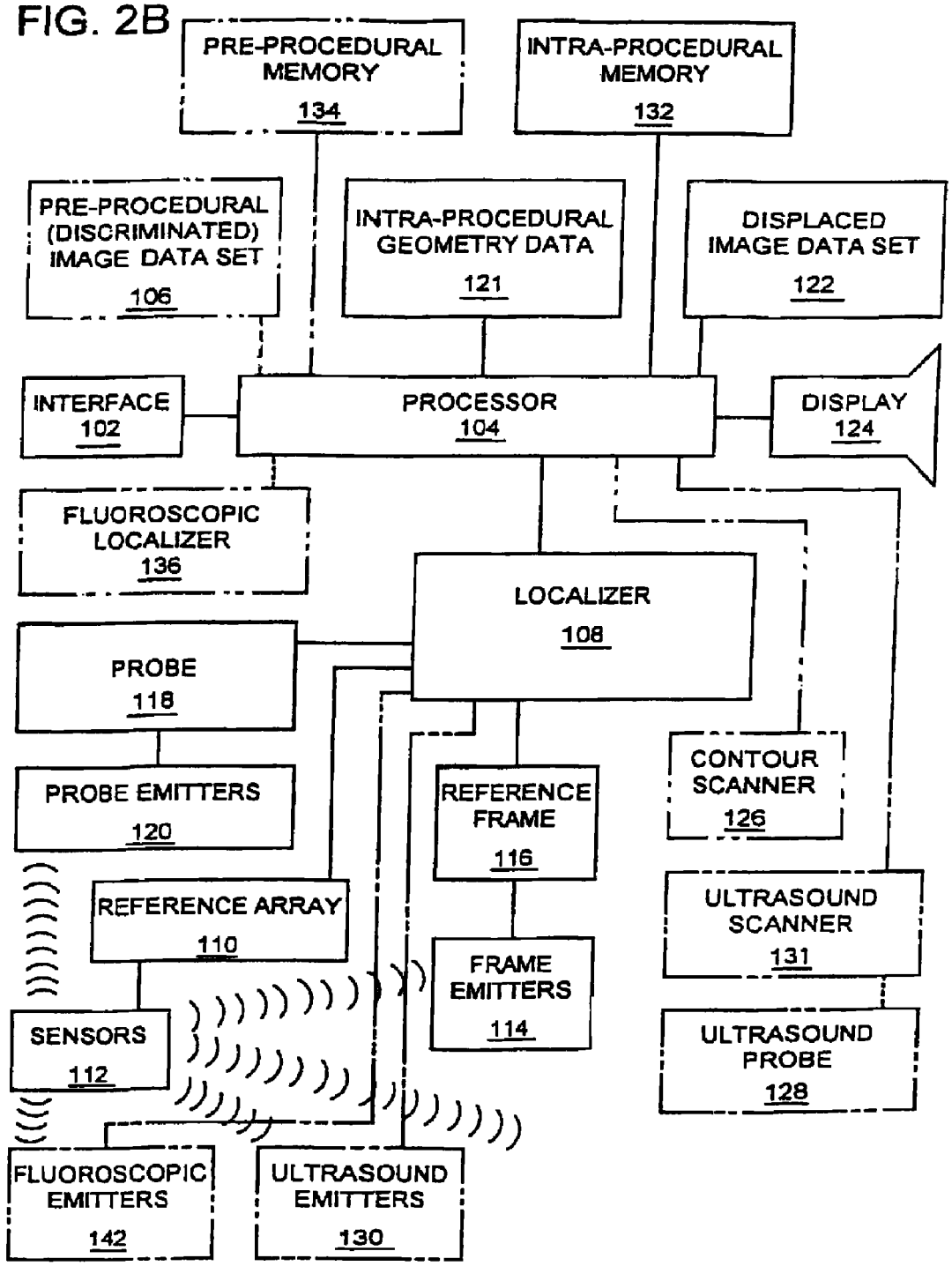

ic applications. No. 10/198,324, filed Jul. 18, 2002, now U.S. Pat. No. 6,978,166, which is a continuation of U.S. patent application Ser. No. 09/398,313, filed on Sep. 20, 1999, now U.S. Pat. No. 6,434,415, which is a continuation of U.S. patent application Ser. No. 08/931,654 filed on Sep. 16, 1997, now U.S. Pat. No. 6,347,240, which is a continuation of U.S. patent application Ser. No. 08/319,615, filed on Oct. 7, 1994, now abandoned.

SYSTEM AND METHOD FOR MODIFYING IMAGES OF A BODY PART

This application is a continuation of U.S. patent application Ser. No. 10/198,324, filed Jul. 18, 2002, now U.S. Pat. No. 6,978,166, which is a continuation of U.S. patent application Ser. No. 09/398,313, filed on Sep. 20, 1999, now U.S. Pat. No. 6,434,415, which is a continuation of U.S. patent application Ser. No. 08/931,654 filed on Sep. 16, 1997, now U.S. Pat. No. 6,347,240, which is a continuation of U.S. patent application Ser. No. 08/319,615, filed on Oct. 7, 1994, now abandoned.

BACKGROUND OF THE INVENTION

The invention relates generally to systems which generate images during medical and surgical procedures, and in particular, a system for generating images during medical and surgical procedures based on a scan taken prior to the procedure.

Image guided medical and surgical procedures comprise a technology by which images, obtained either pre-procedurally or intra-procedurally (i.e., prior to or during a medical or surgical procedure), are used to guide a doctor during the procedure. The recent increase in interest in this field is a direct result of the recent advances in imaging technology, especially in devices using computers to generate three dimensional images of parts of the body, such as computed tomography (CT) or magnetic resonance imaging (MRI).

The majority of the advances in imaging involve devices which tend to be large, encircle the body part being imaged, and are expensive. Although the images produced by these devices depict the body part under investigation with high resolution and good spatial fidelity, their cost usually precludes the dedication of a unit to the performance of procedures. Therefore, image guided surgery is usually performed using images taken preoperatively.

The reliance upon preoperative images has focused image guidance largely to the cranium. The skull, by encasing the brain, serves as a vessel which inhibits changes in anatomy between imaging and surgery. The skull also provides a relatively easy point of reference to which a localization system may be attached so that registration of pre-procedural images to the procedural work space can be done simply at the beginning of the procedure. Registration is defined as the process of relating pre-procedural images of anatomy to the surgical or medical position of the corresponding anatomy. For example, see Ser. No. 07/909,097, now U.S. Pat. No. 5,383,454, the entire disclosure of which is incorporated herein by reference.

This situation of rigid fixation and absence of anatomical movement between imaging and surgery is unique to the skull and intracranial contents and permits a one-to-one registration process as shown in FIG. 1. The position during a medical procedure or surgery is in registration with the pre-procedural image data set because of the absence of anatomical movement from the time of the scan until the time of the procedure. In almost every other part of the body there is ample opportunity for movement which degrades the fidelity of the pre-procedural images in depicting the intra-procedural anatomy. Therefore, additional innovations are needed to bring image guidance to the rest of the body beyond the cranium.

The accuracy of image guided surgery is based on the identification of structures within the body that do not change shape, do not compress, nor deform between the process of imaging and surgery. Such structures are termed "rigid bodies," and the bones of the skeleton satisfy this definition for a rigid body. Bones are commonly a target for medical or surgical procedures either for repair, fusion, or biopsy. Therefore, a technique is needed whereby registration can be performed between the bones or bone fragments (skeletal elements) as depicted pre-procedurally on scans and the position of these same skeletal elements as detected intra-procedurally. This technique must take into account that movement can occur between portions of the skeleton which are not rigidly joined, such as bones connected by a joint, or fragments of a broken bone.

SUMMARY OF THE INVENTION

It is an object of this invention to provide a system which allows registration between multiple skeletal elements depicted in pre-procedural images and detected during surgery.

It is a further object of this invention to provide a system which can localize multiple rigid bodies that move with respect to each other between imaging and a procedure and provide a display during the procedure of the bodies in their displaced positions.

It is another object of this invention to provide a system for use during a medical or surgical procedure on the body, the system generating a display representing the position of two or more body elements during the procedure based on an image data set generated by a scanner prior to the procedure.

It is another object of this invention to provide a system for use during a medical or surgical procedure on a body which modifies the image data set according to the identified relative position of each of the elements during the procedure.

It is another object of this invention to provide a system which generates a display representative of the position of a medical or surgical instrument during a procedure in relation to body elements.

It is a further object of this invention to provide a system for use during image guided medical and surgical procedures which is easily employed by the doctor or surgeon conducting the procedure.

It is another object of this invention to provide a system which determines the relative position of body elements based on the contour of the body elements which, in some cases, avoids the need for exposing the body elements.

It is still another object of this invention to provide a system which employs the projected fluoroscopic images of body elements to determine their relative position.

It is yet a further object of this invention to describe a surgical or medical procedure which employs a display representing the position of body elements during the procedure based on an image data set of the body elements generated prior to the procedure.

It is a further object of this invention to provide a system and method for medical or surgical procedures which allows repositioning of body elements during the procedure and still permits the generation of a display showing the relative position of the body elements.

Other objects and features will be in part apparent and in part pointed out hereinafter.

The invention comprises a system for use during a medical or surgical procedure on a body. The system generates a display representing the position of two or more body elements during the procedure based on an image data set generated by a scanner prior to the procedure, the image data set having reference points for each of the body elements. The reference points of a particular body element have a fixed spatial relation to the particular body element. The system includes means for identifying, during the procedure, the relative position of each of the reference points of each of the body elements to be displayed. The system also includes a processor modifying the image data set according to the identified relative position of each of the reference points during the procedure, as identified by the identifying means. The processor generates a displaced image data set representing the position of the body elements during the procedure. The system also includes a display utilizing the displaced image data set generated by the processor and illustrating the relative position of the body elements during the procedure.

The invention also comprises a method for use during a procedure. The method generates a display representing the position of two or more body elements during the procedure based on an image data set generated prior to the procedure, which image data set has reference points for each of the body elements. The method comprises the steps of:

identifying, during the procedure, the relative position of each of the reference points of each of the body elements to be displayed;

modifying the image data set according to the identified relative position of each of the reference points during the procedure in order to generate a displaced image data set representing the position of the body elements during the procedure; and generating a display based on the displaced image data set illustrating the relative position of the body elements during the procedure.

The invention also comprises a method for use with two or more body elements which each have reference points. The method comprises the steps of:
prior to a procedure:
placing the body elements in a frame to fix their relative position; and
scanning the fixed body elements; and
during the procedure:
placing the body elements in the frame so that the body elements have the same relative position as their position during scanning;
determining the position of reference points on the body elements relative to reference means;
determining the position of a medical or surgical instrument relative to the reference means;
determining the position of the medical or surgical instrument relative to the body elements; and
generating a display based on the pre-procedural scanning illustrating the determined position of the medical or surgical instrument relative to the body elements.

BRIEF DESCRIPTION OF THE DRAWINGS

FIG. 1 is an illustration of the prior art system in which rigid fixation and absence of movement between imaging and surgery permits a one-to-one registration process between the pre-surgical image data set and the position in surgery.

FIG. 2B is a block diagram of one preferred embodiment of a system according to the invention.

Corresponding reference characters indicate corresponding parts throughout the drawings.

DETAILED DESCRIPTION OF THE PREFERRED EMBODIMENTS

Figure 2A:
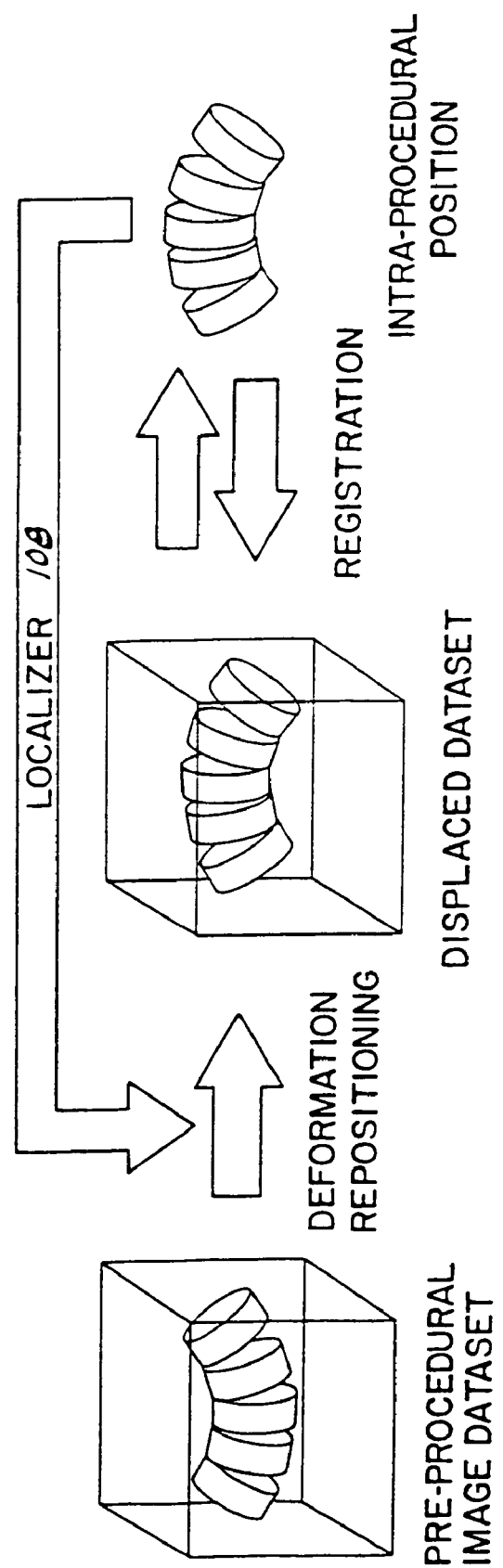
FIG. 2A is an illustration of operation of the invention in which the pre-procedural image data set is modified in accordance with the intra-procedural position in order to generate a displaced data set representative of the intra-procedural position.
Figure 3:
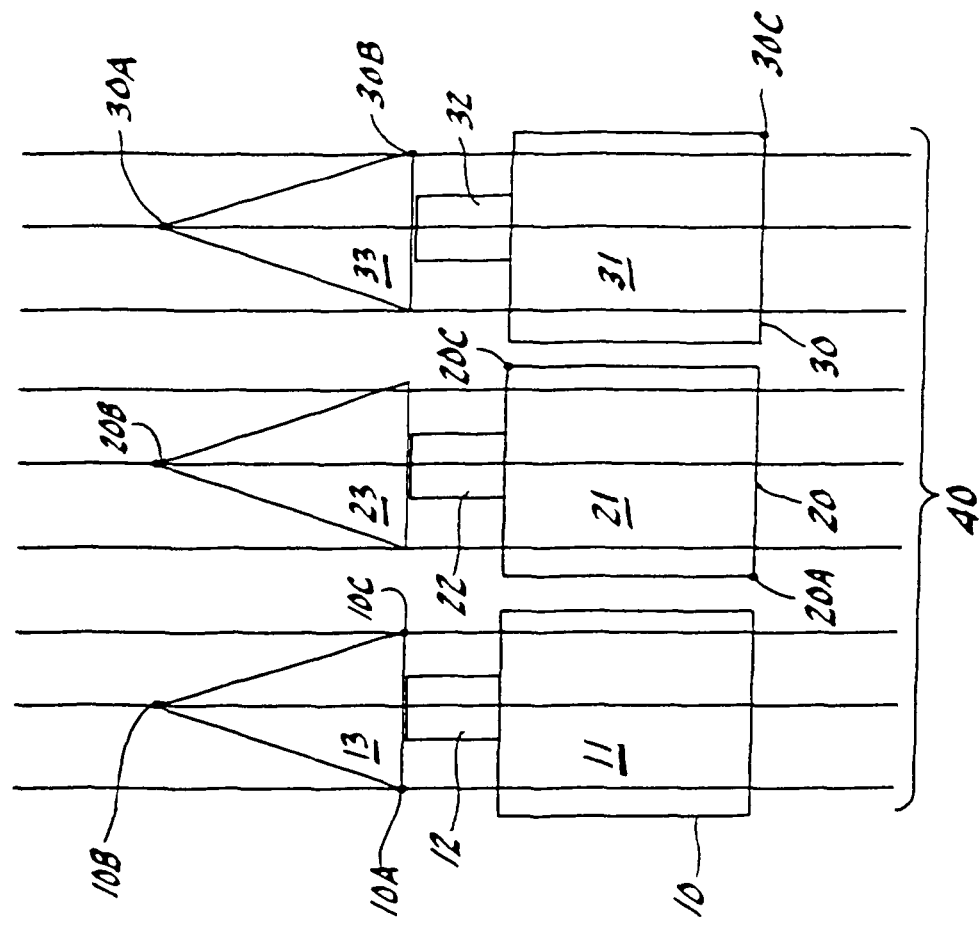
FIG. 3 is an illustration of the pre-procedural alignment of three body elements during scanning.

Referring to FIG. 2A, an overview of operation of one preferred embodiment of the system according to the invention is illustrated. Prior to a particular procedure, the body elements which will be part of the procedure are scanned to determine their alignment. For example, the alignment may be such as illustrated in FIG. 3 wherein body elements 10, 20, and 30 are more or less aligned in parallel. These body elements may be bones or other rigid bodies. In FIG. 3, three-dimensional skeletal elements 10, 20, 30 are depicted in two dimensions as highly stylized vertebral bodies, with square vertebra 11, 21, 31, small rectangular pedicles 12, 22, 32, and triangular spinous processes 13, 23, 33. During imaging, scans are taken at intervals through the body parts 10, 20, 30 as represented in FIG. 3 by nine straight lines generally referred to be reference character 40. At least one scan must be obtained through each of the body elements and the scans taken together constitute a three-dimensional pre-procedural image data set.

FIG. 2B is a block diagram of the system according to the invention. A scanner interface 102 allows a processor 104 to obtain the pre-procedural image data set generated by the scanner and store the data set in pre-procedural image data set memory 106. Preferably, after imaging, processor 104 applies a discrimination process to the pre-procedural image data set so that only the body elements 10, 20, 30 remain in memory 106. If a discrimination process is employed, processor 104 may execute the discrimination process while data is being transferred from the scanner through the scanner interface 102 for storage in memory 106. Alternatively, memory 106 may be used for storing undiscriminated data and a separate memory (not shown) may be provided for storing the discriminated data. In this alternative, processor 104 would transfer the data set from the scanner through scanner interface 102 into memory 106 and then would discriminate the data stored in memory 106 to generate a discriminated image data set which would be stored in the separate memory.

Once the body elements 10, 20, 30 are discriminated from the soft tissue and each defined as a single rigid body, they can be repositioned by software algorithms, well known in the art, to form the displaced image data set. Each of the body elements 10, 20, 30 must have at least three reference points which are selected by the doctor or surgeon and which are visible on the pre-procedural images. These reference points must be able to be indicated with accuracy during the procedure. For body part 10, reference points 10A, 10B, and 10C are located on the spinous process 13; for body part 20, reference points 20A and 20C are located on the vertebra 21 and reference point 20B is located on spinous process 23; and for body part 30, reference points 30A and 30B are located on the spinous process 33 and reference point 30C is located on the vertebra 31. More than one reference point can be selected on each scan through the bone, although the maximal accuracy of registration is achieved by separating the reference points as far as possible. For example, in the case of posterior spinal surgery, it may be preferable to select reference points 10A, 10B, and 10C on the spinous process which is routinely exposed during such surgery. It is contemplated that work station software may allow the manual or automated identification of these same points on the images of the body elements 10, 20, 30. As FIG. 3 is a two-dimensional simplification of a three-dimension process, the reference points will not necessarily be limited to a perfect sagittal plane, as depicted.

After imaging, the skeletal body elements 10, 20, 30 may move with respect to each other at the joints or fracture lines. In the procedure room, such as an operating room or a room where a medical procedure will be performed, after positioning the patient for surgery, the body elements will assume a different geometry, such as the geometry depicted in FIG. 4.

Figure 4:
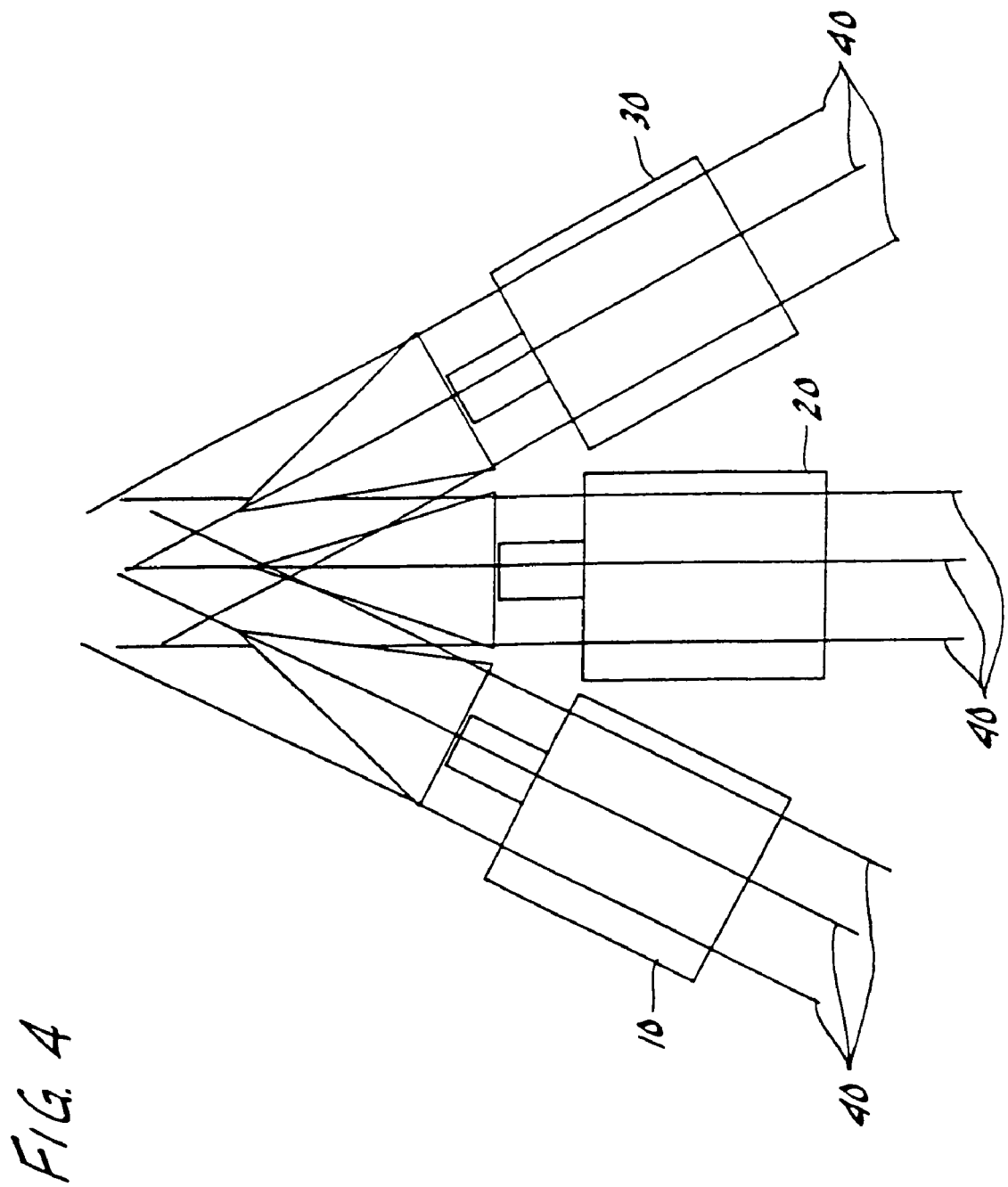
FIG. 4 is an illustration of the intra-procedural alignment of the three body elements of FIG. 3 during surgery.

As a result of this movement, the pre-procedural image data set stored in memory 106, consisting of the scans through the skeletal elements, does not depict the operative position of the skeletal elements, as shown in FIG. 4. However, the shape of the skeletal elements, as depicted by the scans through the element, is consistent between imaging and procedure, as indicated by the lines 40 through each element in FIG. 4. Therefore, the image data set must be modified to depict the current geometry of the skeletal elements. This modification is performed by identifying the location of each reference point of each skeletal element in procedure space. As diagrammatically illustrated in FIG. 2B, a localizer 108 identifies the location and provides this information so that the pre-procedural data set may be deformed or re-positioned into the displaced data set. As a result, the displaced data set is in registration with the intra-procedural position of the elements 10, 20, 30. Once the locations of the reference points are determined by the localizer 108, processor 104, which is a part of the work station, can execute software which repositions the images of the skeletal elements to reflect the position of the actual elements in the procedure room thus forming the displaced set and the registration between the displaced set and the intra-procedural position.

Preferably, a three-dimensional digitizer may be used as the localizer 108 to determine the position and space of the elements 10, 20, 30 during the procedure. In general, the digitizer would include a reference array 110 which receives emissions from a series of emitters. Usually, the emissions consist of some sort of energy, such as light, sound or electromagnetic radiation. The emitters are applied to and positioned in coordination with the elements being localized and the reference array 110 is distant therefrom, determining the position of the emitters. As is apparent, the emitters may be placed distant to the elements and the reference array 110 may be attached to the elements being localized.

Figure 5:
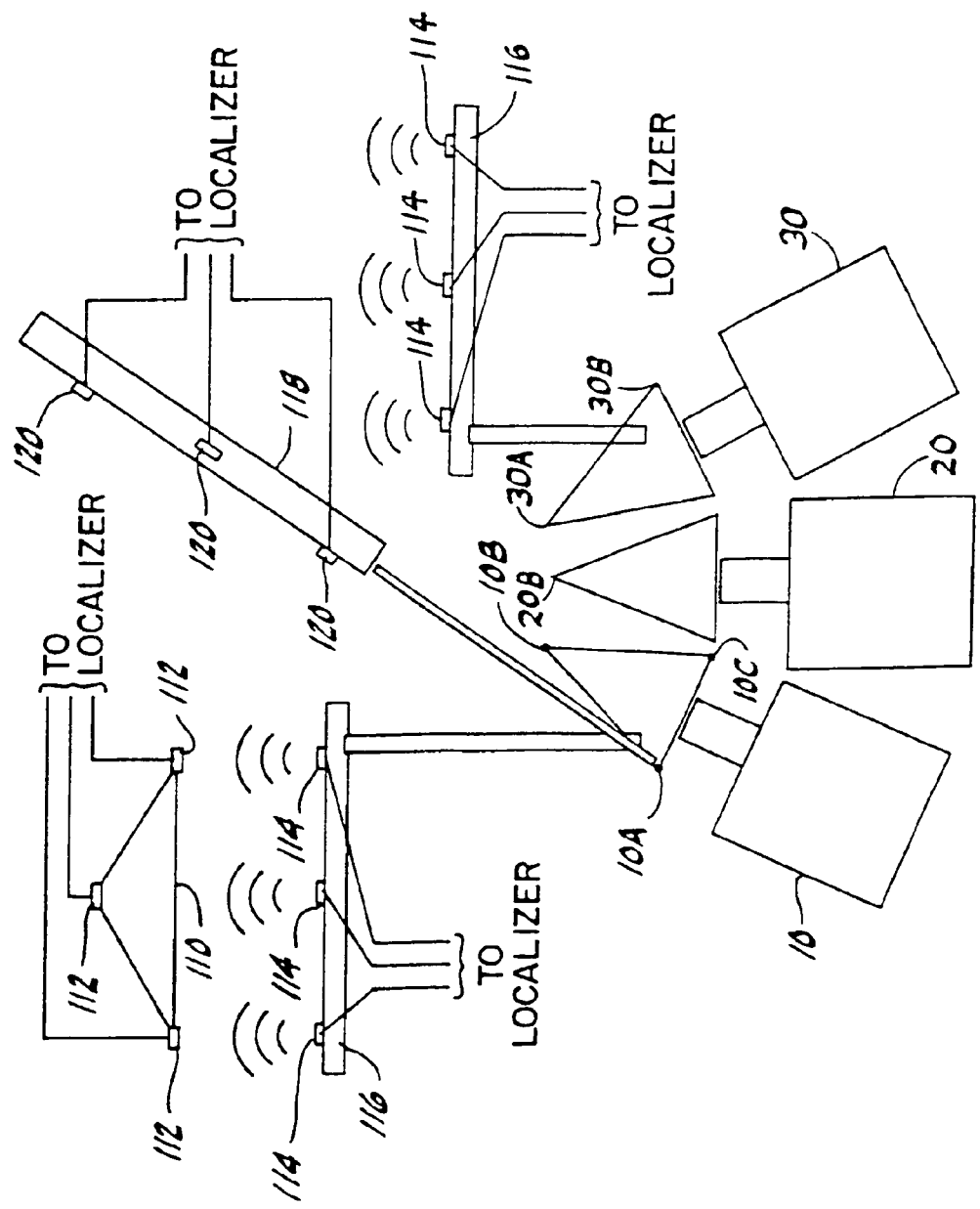
FIG. 5 is an illustration of three body elements, one of which has a reference frame attached thereto, in combination with a probe.

According to one preferred embodiment of the invention as shown in FIG. 5, a reference frame 116 is attached to one of the skeletal elements 10 at the beginning of the procedure. Reference frame 116 is equipped with a plurality of emitters 114 which together define a three-dimensional procedural coordinate system with respect to the skeletal element 10. Emitters 114 communicate with sensors 112 on a reference array 110 located in the procedure room and remote from the reference frame 116 and patient. If the body of the patient is not immobilized during surgery, then multiple reference frames may be required. The three-dimensional procedural coordinate system may alternatively be defined by rigid fixation of the frame emitters 114 directly (or indirectly, for example, to the skin) to the skeletal elements 10, 20, or 30. In either case, the emitters 114 emit a signal which is received by the sensors 112. The received signal is digitized to compute position, for example, by triangulation. Through such information, the localizer 108 or a digitizer which is part of the localizer 108 can determine the exact three-dimensional position of the frame emitters 114 relative to the sensors 112. The sensors 112 are in a fixed position throughout the procedure, as the reference array 110 is fixed in the procedure room to the ceiling or other support. Thereby, localizer 108 or the processor 104 can exactly determine the position of the reference frame 116 relative to the array. The reference frame 116 is free to move except during localization, e.g., activation of the emitters 114 on the reference frame 116 and activation of the probe emitters 120. Emitters 114 of the reference frame 116 are energized to provide radiation to the sensors 112, which radiation is received and generates signals provided to the localizer 108 for determining the position of the frame 116 relative to the array 110.

Next, it is necessary to determine the position of the skeletal element 10 to which the reference frame 116 is affixed. In particular, the position of the skeletal element 10 relative to the reference frame 116 must be determined. After exposure of the reference points 10A, 10B, 10C by surgical dissection, the reference points are touched by the tip of a probe 118 equipped with emitters 120. As each of the reference points 10A, 10B, 10C is touched by the tip of the probe 118, the emitters are energized to communicate with the sensors 112 of reference array 110. This communication permits the localizer 108 to determine the position of the probe 118, thereby determining the position of the tip of the probe 118, thereby determining the position of the reference point 10A on which the tip is positioned. By touching each of the reference points 10A, 10B, 10C on each skeletal element 10, 20, 30 involved in the procedure, and relating them to their corresponding reference points on the images of the same elements, an intra-procedural position data is generated and stored in memory 121. This data is used to derive a transformation which allows the determination of the exact procedural position and orientation of each skeletal element. Using the intra-procedural position of the skeletal elements 10, 20, 30, localizer 108 and processor 104 employ software which manipulates the pre-procedural image data set stored in memory 106 to produce a displaced image data set which is stored in memory 122. The displaced image data set in memory 122 reflects the geometry of the actual elements 10, 20, 30 during the procedure. Processor 104 displays the displaced image data set on display 124 to provide a visual depiction of the relative position of the skeletal elements 10, 20, 30 during the procedure. This image is used by the doctor during the procedure to assist in the procedure. In addition, it is contemplated that an instrument which would be used during the procedure may be modified by the addition of emitters. This modified instrument when moved into the area of the skeletal elements 10, 20, 30 would be activated so that its emitters would communicate with the reference array 110 thereby permitting localizer 108 to determine the instrument's position. As a result, processor 104 would modify display 124 to indicate the position of the instrument, such as by positioning a cursor.

Reference frame 116 allows the patient to be moved during the procedure without the need for re-registering the position of each of the body elements 10, 20, 30. It is assumed that during the procedure, the patient is immobilized so that the body elements are fixed relative to each other. Since the reference frame 116 is affixed to skeletal element 10, movement of the patient results in corresponding movement of the reference frame 116. Periodically, or after each movement of the patient, array emitters 114 may be energized to communicate with the sensors 112 of reference array 110 in order to permit localizer 108 to determine the position of the reference frame 116. Since the reference frame 116 is in a fixed position relative to element 10 and since we have assumed that elements 20 and 30 are in fixed relation to element 10, localizer 108 and/or processor 104 can determine the position of the elements. From this position, a displaced image data set memory can be created for display on display 124.

An alternative to touching the reference points A, B, C with the tip of the probe 118 would be to use a contour scanner 126. Such a device, using some form of energy such as sound or light which is emitted, reflected by the contour and sensed, would allow the extraction of a contour of the skeletal elements 10, 20, 30, thus serving as a multitude of reference points which would allow registration to occur. The registration process is analogous to the process described for ultrasound extracted contours below.

In certain situations, markers may be used on the skin surface as reference points to allow the transformation of the pre-procedural image data set into the displaced image data set. Reciprocally, skin surface fiducials applied at the time of imaging can be used to re-position the body to match the geometry during imaging and is described below.

Localization of skeletal elements 10, 20, 30 may be desired without intra-procedural exposure of the reference points A, B, C on those skeletal elements. Examples wherein the spine is minimally exposed include percutaneous biopsy of the spine or discectomy, spinal fixation, endoscopy, percutaneous spinal implant insertion, percutaneous fusion, and insertion of drug delivery systems. In this situation, localization of reference points on the skeletal elements must be determined by some form of imaging which can localize through overlying soft tissue. There are currently two imaging techniques which are available to a surgeon in the operating room or a doctor in a procedure room which satisfy the needs of being low cost and portable. Both imaging techniques, ultrasonography and radiography, can produce two- or three-dimensional images which can be employed in the fashion described herein to register a three-dimensional form such as a skeletal element.

Figure 6:
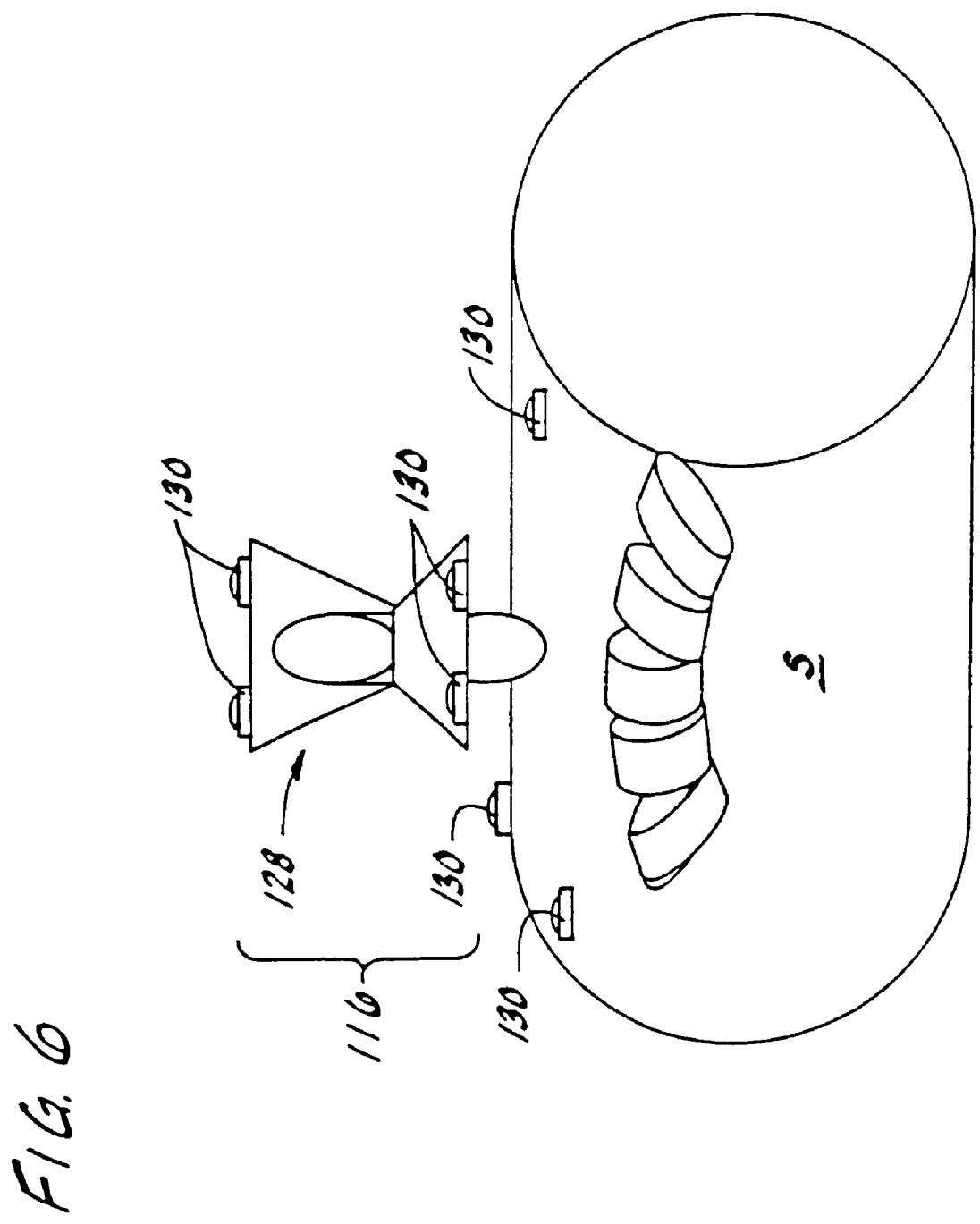
FIG. 6 is an illustration showing ultrasound registration according to the invention in which emitters are attached to the patient's body.

As described in U.S. Pat. Nos. 5,851,183 and 5,871,445, the entire disclosures of which are incorporated herein by reference, the coupling of a three-dimensional digitizer to a probe of an ultrasound device affords benefits in that a contour can be obtained which can be related directly to a reference system that defines three-dimensional coordinates in the procedural work space. In the context of the present invention, a patient is imaged prior to a procedure to generate a pre-procedural image data set which is stored in memory 106. In the procedure room, the patient's body is immobilized to stabilize the spatial relationship between the skeletal elements 10, 20, 30. A reference system for the body is established by attaching a reference array 110 to one of the skeletal elements or by otherwise attaching emitters to the patient or skeletal elements as noted above. For example, this could be performed by using the percutaneous placement of a reference system similar to the one described above, radiopaque markers screwed into the elements or by placing emitters 130 directly on the skins, as illustrated in FIG. 6, based on the assumption that the skin does not move appreciably during the procedure or in respect to the axial skeleton.

An ultrasound probe 128 equipped with at least three emitters 130 is then placed over the skeletal element of interest. The contour (which can be either two- or three-dimensional) of the underlying bone/soft tissue interface is then obtained using the ultrasound probe 128. This contour of the underlying bone can be expressed directly or indirectly in the procedural coordinates defined by the reference system. Emitters 130 communicate with sensors 112 of reference array 110 to indicate the position of the ultrasound probe 128. An ultrasound scanner 131 which energizes probe 128 determines the contour of the skeletal element of interest being scanned. This contour information is provided to processor 104 for storage in contour memory 132.

The intra-procedural contour stored in memory 132 is then compared by a contour matching algorithm to a corresponding contour extracted from the pre-operative image data set stored in memory 106. Alternatively, a pre-procedural contour data set may be stored in memory 134 based on a pre-procedural ultrasound scan which is input into memory 134 via scanner interface 102 prior to the procedure. This comparison process continues until a match is found for each one of the elements. Through this contour matching process, a registration is obtained between the images of each skeletal element and the corresponding position of each element in the procedural space.

In certain instances, the ultrasound registration noted above may not be applicable. For example, ultrasound does not penetrate bone, and the presence of overlying bone would preclude the registration of an underlying skeletal element. Further, the resolution of ultrasound declines as the depth of the tissue being imaged increases and may not be useful when the skeletal element is so deep as to preclude obtaining an accurate ultrasonically generated contour. In these circumstances, a radiological method is indicated, which utilizes the greater penetrating power of x-rays.

Figure 7:
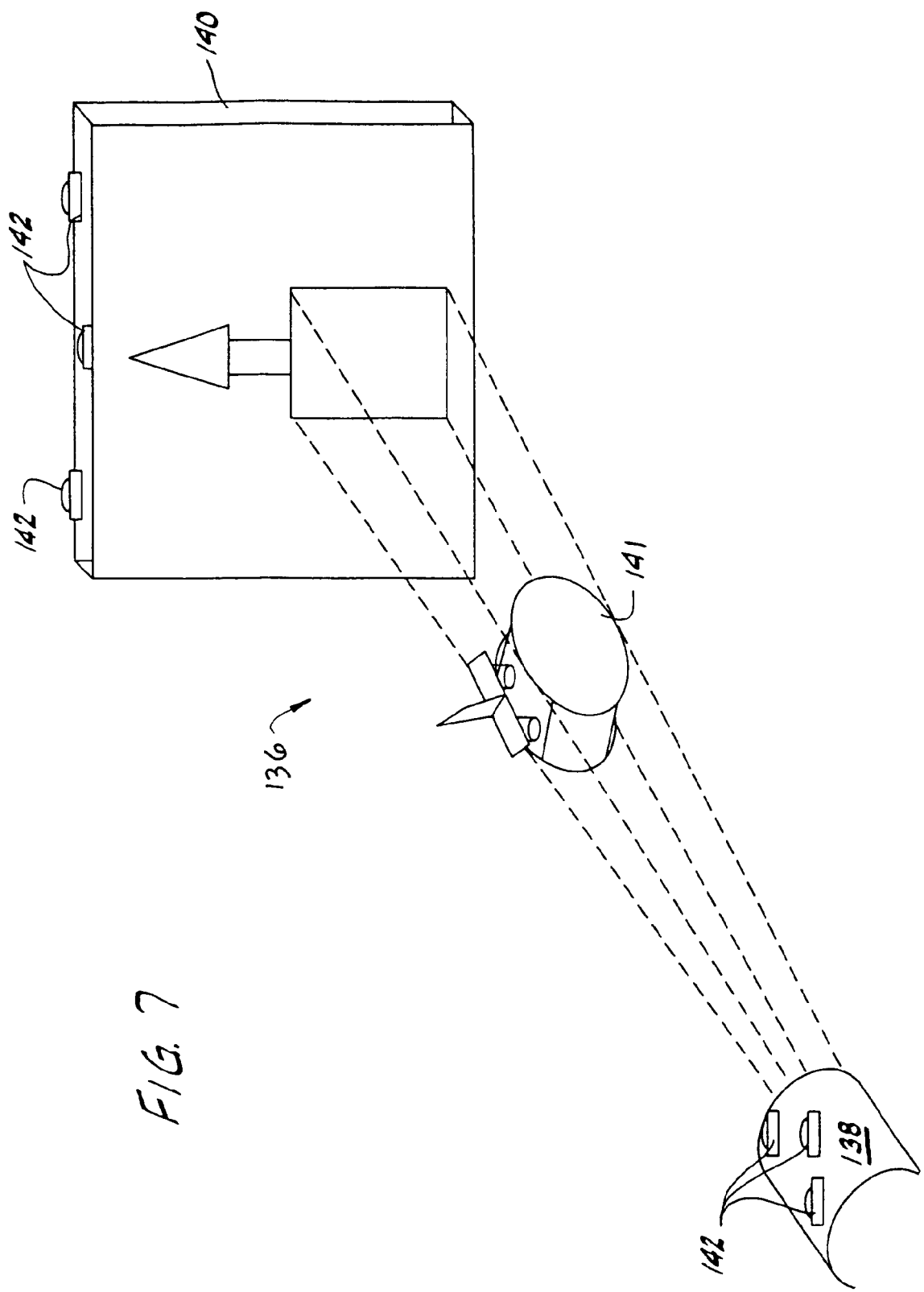
FIG. 7 is an illustration of a fluoroscopic localizer according to the invention for providing projections of an image of the body elements.

Pre-operative imaging occurs as usual and the skeletal elements are discriminated from the soft tissue in the image data set as above. In particular, a CT scan of the skeletal elements 10, 20, 30 is taken prior to the procedure. Processor 104 may then discriminate the skeletal elements. Next, the patient is immobilized for the procedure. A radiograph of the skeletal anatomy of interest is taken by a radiographic device equipped with emitters detectable by the digitizer. For example, a fluoroscopic localizer 136 is illustrated in FIG. 7. Localizer 136 includes a device which emits x-rays such as tube 138 and a screen 140 which is sensitive to x-rays, producing an image when x-rays pass through it. In general, this screen is referred to as a fluoroscopic plate. Emitters 142 may be positioned on the tube 138, or on the fluoroscopic plate 140 or on both. For devices in which the tube 138 is rigidly supported relative to the plate 140, emitters need only be provided on either the tube or the plate. Alternatively, the reference array 110 may be attached to the tube or the plate. By passing x-rays through the skeletal element 141 of interest, a two-dimensional image based on bone density is produced and recorded by the plate. The image produced by the fluoroscopic localizer 136 is determined by the angle of the tube 138 with respect to the plate 140 and the position of the skeletal elements therebetween. Fluoroscopic localizer 136 includes a processor which digitizes the image on the plate 140 and provides the digitized image to processor 104 for storage in memory 106. Processor 104 may simulate the generation of this two-dimensional x-ray image by creating a two-dimensional projection of the three-dimensional skeletal elements that have been discriminated in the image data set stored in memory 106. In order to form the displaced data set and thus achieve registration, an iterative process is used which re-positions the images of the skeletal elements such that a two-dimensional projection through the displaced data set matches the actual radiographic image. The described process can utilize more than one radiographic image. Since the processor 104 is also aware of the position of the fluoroscopic localizers because of the emitters 142 thereon, which are in communication with localizer 108, the exact position of the skeletal elements during the procedure is determined.

The above solutions achieve registration by the formation of a displaced image data set stored in memory 122 which matches the displacement of the skeletal elements at the time of the procedure. An alternative technique to achieve registration is to ensure that the positions of the skeletal elements during the procedure are identical to that found at the time of imaging. This can be achieved by using a frame that adjusts and immobilizes the patient's position. In this technique, at least three markers are placed on the skin prior to imaging. These markers have to be detectible by the imaging technique employed and are called fiducials. A multiplicity of fiducials is desirable for improving accuracy.

During the procedure, the patient's body is placed on a frame that allows precise positioning. Such frames are commonly used for spinal surgery and could be modified to allow their use during imaging and could be used for repositioning the patient during the procedure. These frames could be equipped with drive mechanisms that allow the body to be moved slowly through a variety of positions. The fiducials placed at the time of imaging are replaced by emitters. By activating the drive mechanism on the frame, the exact position of the emitters can be determined during the procedure and compared to the position of the fiducials on the pre-procedural image data set stored in memory 106. Once the emitters assume a geometry identical to the geometry of the fiducials of the image data set, it is considered that the skeletal elements will have resumed a geometric relationship identical to the position during the pre-procedural scan, and the procedure can be performed using the unaltered image data set stored in memory 106.

In general, instrumentation employed during procedures on the skeleton is somewhat different than that used for cranial applications. Rather than being concerned with the current location, surgery on the skeleton usually consists of placing hardware through bones, taking a biopsy through the bone, or removing fragments. Therefore, the instrumentation has to be specialized for this application.

Figure 8:
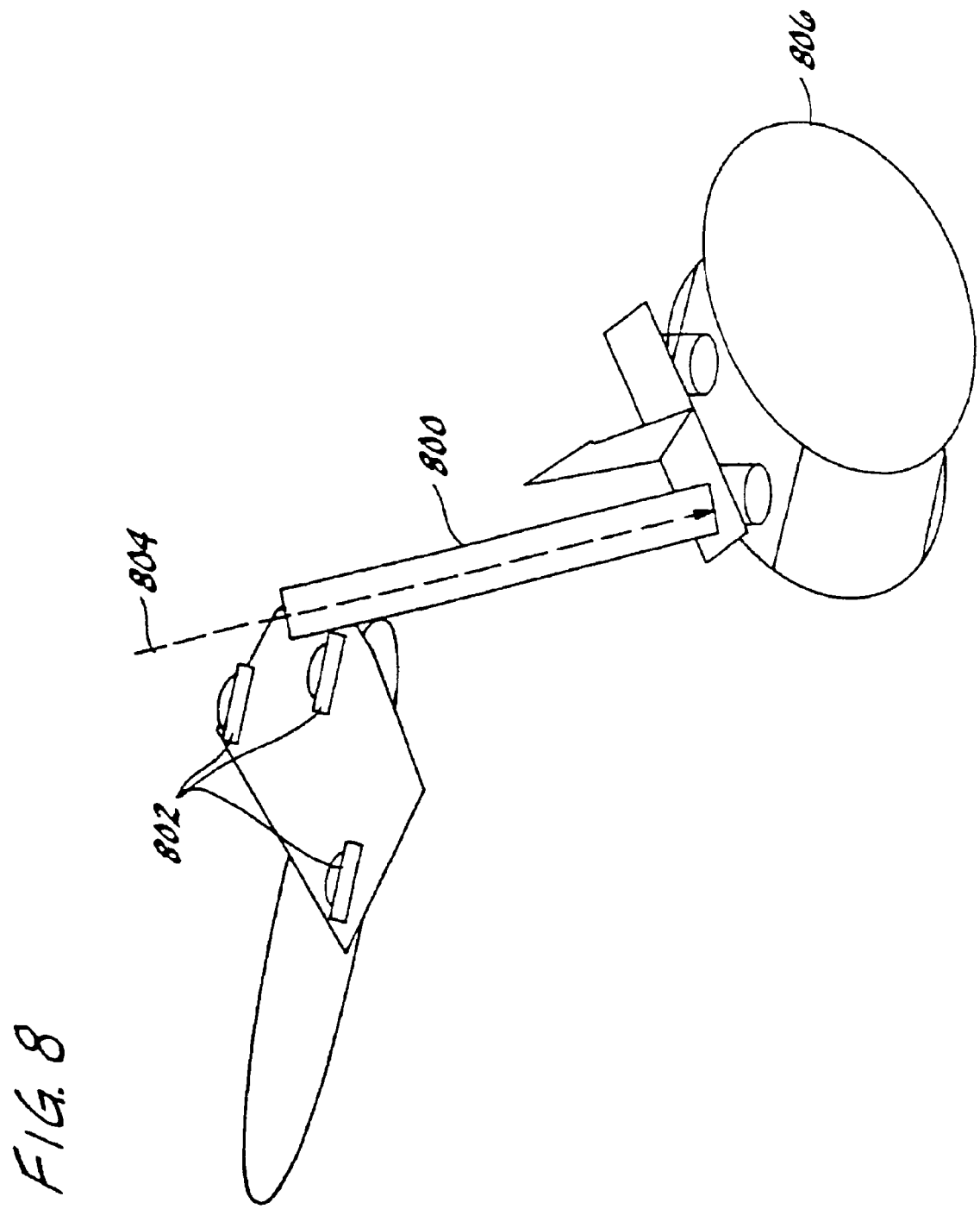
FIG. 8 is an illustration of a drill guide instrument of the invention wherein the position of a drill guide relative to the body elements may be displayed.

One instrument that is used commonly is a drill. By placing emitters on a surgical drill, and by having a fixed relationship between the drill body and its tip (usually a drill bit), the direction and position of the drill bit can be determined. At least three emitters would be needed on the drill, as most drills have a complex three-dimensional shape. Alternatively, emitters could be placed on a drill guide tube 800 having emitters 802, and the direction 804 of the screw being placed or hole being made could be determined by the digitizer and indicated on the image data set (see FIG. 8). The skeletal element 806 would also have emitters thereon to indicate its position.

Besides modification of existing instrumentation, new instrumentation is required to provide a reference system for surgery as discussed above. These reference frames, each equipped with at least 3 emitters, require fixation to the bone which prevents movement or rotation.

Figure 9:
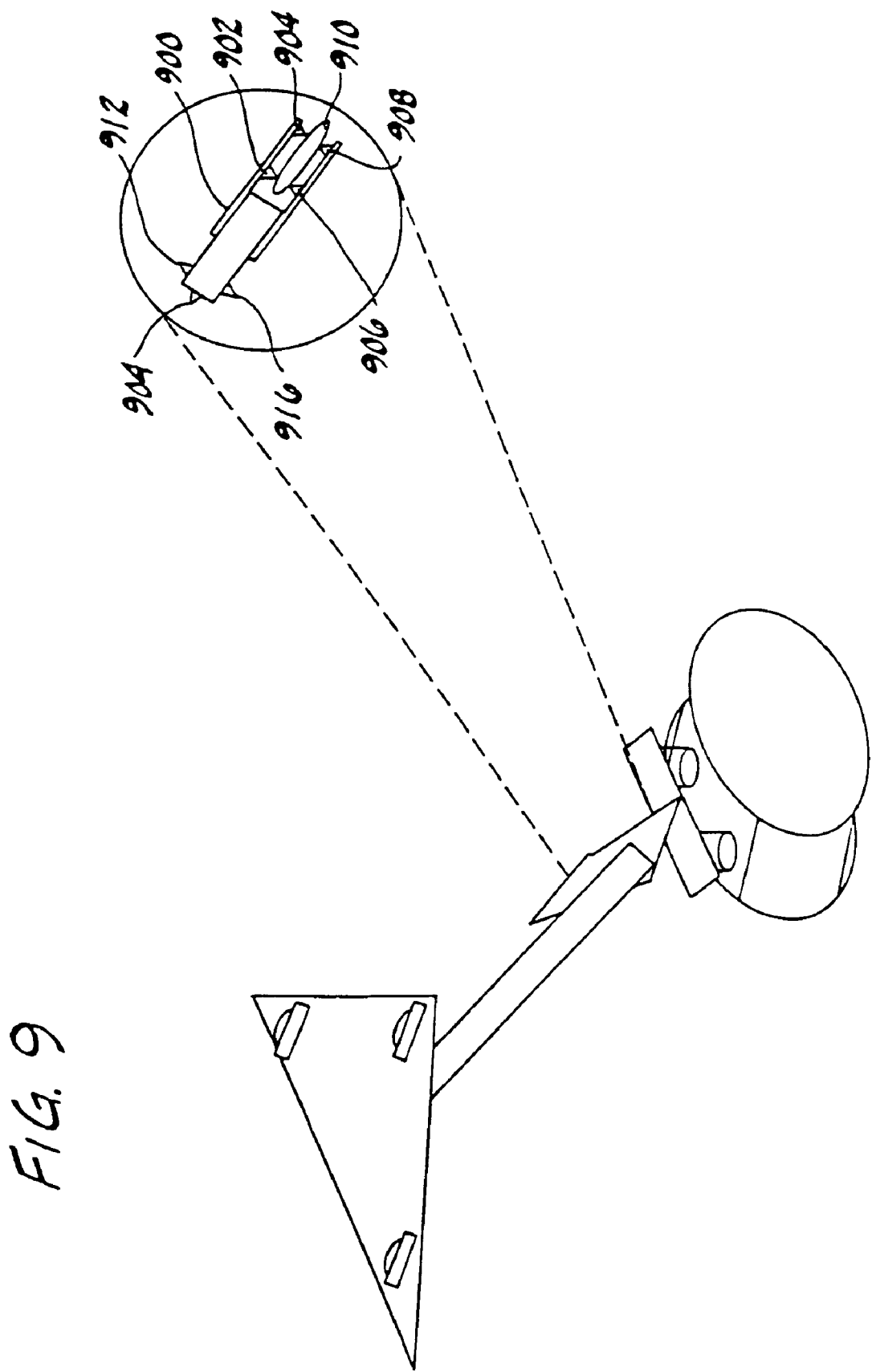
FIGS. 9 and 10 illustrate a clamped reference frame and a wired reference frame, respectively.

For open surgery, a clamp like arrangement, as depicted in FIG. 9, can be used. A clamp 900 is equipped with at least two points 902, 904, 906, 908 which provide fixation to a projection 910 of a skeletal element. By using at least two point fixation the clamp 900, which functions as a reference frame, will not rotate with respect to the skeletal element. The clamp includes emitters 912, 914, 916 which communicate with the array to indicate the position of the skeletal element as it is moved during the procedure.

Figure 10:
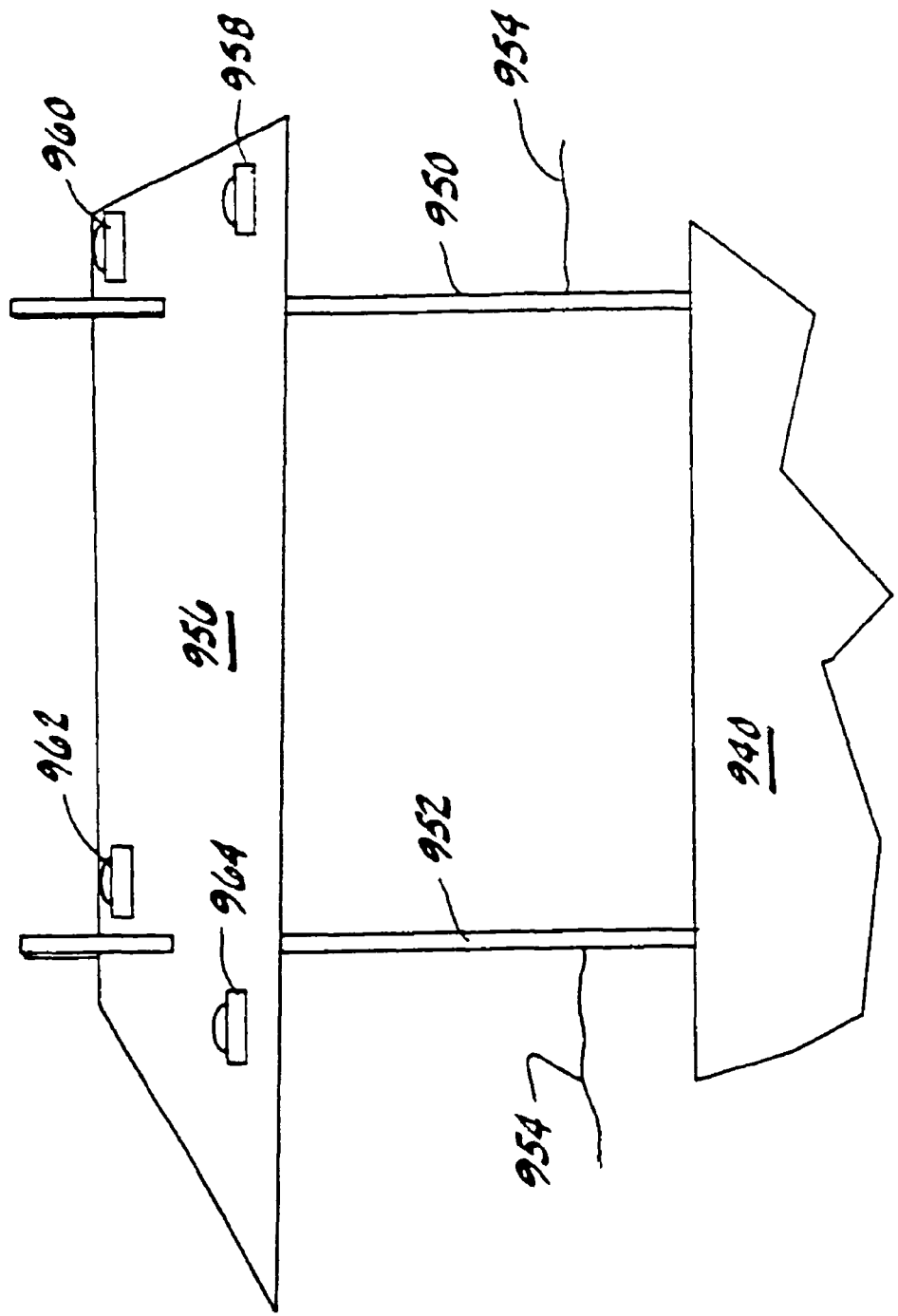

Many procedures deal with bone fragments 940 which are not exposed during surgery, but simply fixated with either wires or screws 950, 952 introduced through the skin 954. FIG. 10 depicts a reference platform 956 attached to such wires or screws 950, 952 projecting through the skin 954. The platform 956 includes a plurality of emitters 958, 960, 962, 964 which communicate with the array to indicate the position of the bone fragment 940 as it is moved during the procedure.

The reference frame can be slipped over or attached to the projecting screws or wires to establish a reference system. Alternatively, the frame can be attached to only one wire, as long as the method of attachment of the frame to the screw or wire prevents rotation, and that the wire or screw cannot rotate within the attached skeletal element.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

What is claimed is:

1. A system for use during a medical or surgical procedure on a portion of a body, said system for use with a discriminated image data set identifying skeletal elements of the portion of the body and representing a position and a geometry of the skeletal elements of the portion of the body; said system comprising:
   a memory for storing the discriminated image data set;
   an imaging device for producing, during the procedure, a density image of the portion of the body;
   a processor modifying the discriminated image data set stored in the memory according to the density image, said processor generating a displaced image data set representing the position and geometry of the skeletal elements of the portion of the body during the procedure; and
   a display utilizing the displaced image data set illustrating the position and geometry of the skeletal elements of the portion of the body during the procedure.

2. The system of claim 1 wherein the imaging device comprises a reference array for providing a reference and a device for determining the position of one or more reference points of the body element to be displayed relative to the reference array.

3. The system of claim 2 wherein the imaging device is a radiographic device.

4. The system of claim 3 wherein the radiographic device is a fluoroscopic device comprising a fluoroscopic tube and a fluoroscopic plate.

5. The system of claim 4 wherein the fluoroscopic tube is fixed in relation to the fluoroscopic plate so that a particular portion of the body may be positioned therebetween for producing the density image of such particular portion of the body during the procedure and wherein the processor compares the density image of such particular portion of the body during the procedure to the position of the skeletal elements of the portion of the body as represented by the discriminated image data set.

6. The system of claim 4 wherein the fluoroscopic tube is fixed in relation to a fluoroscopic plate so that a particular portion of the body may be positioned therebetween for producing the density image of such particular portion of the body during the procedure and wherein the processor compares the density image of such particular portion of the body during the procedure to the geometry of the skeletal elements of the portion of the body as represented by the discriminated image data set.

7. The system of claim 4 wherein said fluoroscopic tube has sensors thereon in communication with the reference array and wherein the determining device is adapted to determine the position of the tube relative to the reference array whereby the position of the density image of the portion of the body can be determined.

8. The system of claim 4 wherein said fluoroscopic plate has sensors thereon in communication with the reference array and wherein the determining device is adapted to determine the position of the plate relative to the reference array whereby the position of the density image of the portion of the body can be determined.

9. The system of claim 4 wherein said reference array has sensors thereon in communication with the fluoroscopic device and wherein the determining device is adapted to determine the position of the fluoroscopic device relative to the reference array whereby the position of the density image of the portion of the body can be determined.

10. The system of claim 1 wherein the imaging device is a radiographic device.

11. The system of claim 10 wherein the radiographic device is a fluoroscopic device comprising a fluoroscopic tube and a fluoroscopic plate.

12. The system of claim 11 wherein the fluoroscopic tube is fixed in relation to the fluoroscopic plate so that a particular portion of the body may be positioned therebetween for producing the density image of such particular portion of the body during the procedure and wherein the processor compares the density image of such particular portion of the body during the procedure to the position of the skeletal elements of the portion of the body as represented by the discriminated image data set.

13. The system of claim 11 wherein the fluoroscopic tube is fixed in relation to a fluoroscopic plate so that a particular portion of the body may be positioned therebetween for producing the density image of such particular portion of the body during the procedure and wherein the processor compares the density image of such particular portion of the body during the procedure to the geometry of the skeletal elements of the portion of the body as represented by the discriminated image data set.

14. The system of claim 11 wherein said fluoroscopic tube has sensors thereon in communication with the reference array and wherein the determining device is adapted to determine the position of the tube relative to the reference array whereby the position of the density image of the portion of the body can be determined.

15. The system of claim 11 wherein said fluoroscopic plate has sensors thereon in communication with the reference array and wherein the determining device is adapted to determine the position of the plate relative to the reference array whereby the position of the density image of the portion of the body can be determined.

16. The system of claim 1 wherein the processor modifies the discriminated image data set to generate the displaced data set using an iterative process such that a two-dimensional projection through the displaced image data set matches the density image during the procedure.

17. A system for displaying relative positions of first and second body portions during a procedure on a body, the system for use with a discriminated image data subset representing a position and geometry of the first and second body portions; said image data subset defining a position and geometry of the first and second body portions, the image data subset further having a plurality of data points correlatable to a plurality of reference points for the first and second body portions, the position of reference points of a particular body portion relative to the data points for that particular body portion being known; said system comprising:
a memory for storing the discriminated image subdata set;
a reference system determining, during the procedure, the position of the reference points of the first body portion of the discriminated image data subset relative to the reference points of the second body portion of the discriminated image data subset;
a radiographic device producing a two-dimensional radiographic image of the first and second body portions during the procedure which includes the identification of reference points of the first and second body portions;
wherein the processor further digitizes the radiographic image and generates a displaced image data set representing the position of the first and second body portions during the procedure by modifying the image data subset stored in the memory using an iterative process such that a two-dimensional projection through the displaced image data set substantially matches the radiographic image; and
a display utilizing the displaced image data set to display the relative position of the first and second body portions during the procedure.

18. The system of claim 17 wherein the reference system comprises a plurality of reference frames in communication with a reference array; wherein at least one of the plurality of reference frames is configured to be fixed in relation to a separate portion of the body of the first and second body portions and each of the plurality of reference frames being correlatable to the position of the reference points for each separate portion of the body with which each of the plurality of reference frames is fixed in relation to.

19. The system of claim 18, wherein the radiographic device is equipped with sensors that are in communication with the plurality of reference frames whereby the position of the sensors relative to the reference array during the procedure is determined, whereby the position of the radiographic device is determined and whereby the position of the first and second body portions during the procedure is determined.

20. The system of claim 19, wherein the processor translates the image data subset from the position of the first and second body portions as indicated in the image data subset to the position of the first and second body portions during the procedure so that the displaced image data set consists of the translated image data subset.

21. The system of claim 18, wherein a position of the plurality of reference frames is known in relation to one of the body portions, and the reference system determines the position of the plurality of reference frames relative to the reference array so that the body may be moved during the procedure while the first and second body portions remain in fixed relation to each other and in known relation to the plurality of reference frames so that the system can determine the position of the first and second body portions after movement without re-determining the relative position of each of the reference points of the first and second body portions.

22. The system of 17, wherein the radiographic device is a fluoroscopic device comprising a fluoroscopic tube and a fluoroscopic plate so that the first and second body portions may be positioned therebetween during the procedure.

23. The system of claim 22, wherein the fluoroscopic device determines a position of the two-dimensional radiographic image of the first and second body portions during the procedure, and wherein the processor compares the position of the two-dimensional radiographic image of the first and second body portions during the procedure to the position of the first and second body portions as represented by the image data subset.

24. The system of claim 22, wherein the fluoroscopic device determines a position of the two-dimensional radiographic image based on a density of the first and second body portions during the procedure, and wherein the processor compares the position of the two-dimensional radiographic image based on the density of the first and second body portions during the procedure to the position of the first and second body portions as represented by the image data subset.

25. The system of claim 22 wherein the radiographic device produces a two-dimensional radiographic image based on a density of the first and second body portions.

26. The system of claim 17 wherein the processor further creates a two-dimensional projection image of the first and second body portions that have been discriminated in the image data subset.

27. A method for use during a procedure, said method for use with a discriminated image data set identifying one or more body portions and representing a position and a geometry of the one or more body portions, the method comprising:
    storing the discriminated image data set in a memory;
    producing a two-dimensional image based on density of the one or more body portions during the procedure;
    producing a displaced image data set by modifying the discriminated image data set stored in the memory such that a two-dimensional projection through the displaced image data set matches the two-dimensional image during the procedure; and
    generating a display based on the displaced image data set illustrating the position of the one or more body portions during the procedure.

28. The method of claim 27, further comprising the step of simulating the generation of a two-dimensional image of the body portions by creating a two-dimensional projection image of the one or more body portions in the discriminated image data set.

29. The method of claim 27 wherein the step of producing the displaced data set includes modifying the discriminated image data set based on an iterative process based on the two-dimensional density image.

30. The method of claim 27 further comprising the step of determining the position of the body portions during the procedure.

31. The method of claim 27 wherein the step of generating a display based on the displaced image data set further comprises the substep of illustrating the geometry of the one or more body portions during the procedure.

32. A method for use during a medical or surgical procedure on one or more body portions, said method for use with a discriminated image data set representing the position and geometry of the one or more body portions; said method comprising:
    storing the discriminated image data set in a memory;
    producing, during the procedure, a density image of the one or more body portions to be displayed;
    generating a displaced image data set representing the position and geometry of the one or more body portions during the procedure, by comparing the density image of the one or more body portions during the procedure to the discriminated image data set stored in the memory of the one or more body portions and modifying the discriminated image data set according to the density image of the one or more body portions during the procedure; and
    displaying the displaced image data set thereby illustrating the position and geometry of the one or more body portions during the procedure.

33. The method of claim 32 wherein the step of producing a density image further comprises the substep of determining the position of one or more reference points of the one or more body portions to be displayed relative to a reference array.

34. The method of claim 32 wherein the step of producing the density image further comprises the substep of determining the position of a fluoroscopic tube and a fluoroscopic plate relative to a reference array and thereby determining the position of the density image of the one or more body portions.

35. The method of claim 32 wherein a reference array has sensors thereon in communication with a fluoroscopic device and wherein the step of producing the density image further comprises the substep of determining a position of the fluoroscopic device relative to the reference array whereby the position of the density image of the one or more body portions can be determined.

36. The method of claim 32, further comprising the step of comparing the density image of the one or more body portions during the procedure to the position of the one or more body portions as represented by the discriminated image data set.

37. The method of claim 32, further comprising the step of comparing the density image of the one or more body portions during the procedure to the geometry of the one or more body portions as represented by the discriminated image data set.

38. The method of claim 32, further comprising the steps of:
    digitizing the density image;
    generating a two-dimensional image by creating a two-dimensional projection image of the one or more body portions in the discriminated image data set; and
    generating a displaced image data set representing the position of the one or more body portions during the procedure by modifying the discriminated image data set using an iterative process such that the two-dimensional image matches the density image.

39. The method of claim 32, further comprising the step of creating a two-dimensional projection image of the body portion in the discriminated image data set.

40. A system for use during a medical or surgical procedure on a portion of the body, said system for use with a discriminated image data set identifying the portion of the body and representing a position and a geometry of the portion of the body; said system comprising:
    a memory for storing the discriminated image data set;
    means for producing, during the procedure, a density image of the portion of the body;
    a processor modifying the discriminated image data set stored in the memory according to the density image, said processor generating a displaced image data set representing the position and geometry of the portion of the body during the procedure; and
    a display utilizing the displaced image data set illustrating the position and geometry of the portion of the body during the procedure.

* * * * *